United States Patent
Wang et al.

(10) Patent No.: US 12,428,369 B2
(45) Date of Patent: Sep. 30, 2025

(54) CRYSTAL FORM OF AROMATIC VINYL DERIVATIVES, AND PREPARATION METHOD THEREFOR AND USE THEREOF

(71) Applicant: GUANGZHOU MAXINOVEL PHARMACEUTICALS CO., LTD., Guangdong (CN)

(72) Inventors: Yuguang Wang, Guangdong (CN); Nong Zhang, Guangdong (CN); Pingjing Zhang, Guangdong (CN)

(73) Assignee: GUANGZHOU MAXINOVEL PHARMACEUTICALS CO., LTD., Guangdong (CN)

( * ) Notice: Subject to any disclaimer, the term of this patent is extended or adjusted under 35 U.S.C. 154(b) by 469 days.

(21) Appl. No.: 17/912,142

(22) PCT Filed: Mar. 2, 2021

(86) PCT No.: PCT/CN2021/078640
§ 371 (c)(1),
(2) Date: Sep. 16, 2022

(87) PCT Pub. No.: WO2021/185072
PCT Pub. Date: Sep. 23, 2021

(65) Prior Publication Data
US 2023/0115605 A1    Apr. 13, 2023

(30) Foreign Application Priority Data

Mar. 17, 2020 (CN) .......................... 202010185597.7

(51) Int. Cl.
C07C 229/22 (2006.01)
C07C 227/42 (2006.01)

(52) U.S. Cl.
CPC .......... *C07C 229/22* (2013.01); *C07C 227/42* (2013.01); *C07B 2200/13* (2013.01)

(58) Field of Classification Search
CPC ................................................... C07C 229/22
See application file for complete search history.

(56) References Cited

FOREIGN PATENT DOCUMENTS

| CN | 104230907 A | 12/2014 | |
|---|---|---|---|
| CN | 107573332 A | 1/2018 | |
| CN | 109988144 A | 7/2019 | |
| WO | WO-2019128918 A1 * | 7/2019 | ........... A61K 31/198 |

OTHER PUBLICATIONS

First Office Action issued on Jun. 26, 2023 for application No. CN202110316849X with English translation attached.
Extended European Search Report issued on Mar. 25, 2024, for Application No. EP21772080.4.
Office Action issued on Jul. 10, 2024 for Taiwanese Application No. 110109247 with English translation.
Written Opinion of the International Searching Authority issued on Jun. 8, 2021 for International Patent Application No. PCT/CN2021/078640 with English translation attached.
International Search Report issued on Oct. 28, 2021 for International Patent Application No. PCT/CN2021/078640 with English translation attached.
Carter, et al.; "PD-1:PD-L inhibitory pathway affects both CD4+ and CD8+ T cells and is overcome by IL-2"; Wyeth-Genetics Institute, Cambridge, USA; Eur. J. Immunol., 2002, 32(3), 634-643.
Dec. 24, 2024, First Office Action issued in Japanese Application No. 2022-555895.
Handbook of Organic Compound Crystal Production, 2008, P57-61.
Drug and Crystal Polymorphism, Journal of human environmental engineering, 2002, P310-311.

* cited by examiner

*Primary Examiner* — John S Kenyon
*Assistant Examiner* — Rehana Ismail
(74) *Attorney, Agent, or Firm* — Nath, Goldberg & Meyer; Joshua B. Goldberg

(57) ABSTRACT

Disclosed in the present invention are a crystal form of aromatic vinyl derivatives, and a preparation method therefor and the use thereof. Specifically disclosed in the present invention are crystal form A, crystal form B and crystal form C of a compound as shown in formula I. The crystal forms of the present invention have a good stability, are less hygroscopic and are easy to prepare, and have an important value in terms of the optimization and development of drugs.

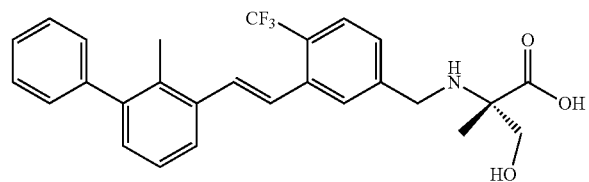

21 Claims, 12 Drawing Sheets

CRYSTAL FORM OF AROMATIC VINYL DERIVATIVES, AND PREPARATION METHOD THEREFOR AND USE THEREOF

This is a National Phase Application filed under 35 U.S.C. 371 as a national stage of PCT/CN2021/078640, filed Mar. 2, 2021, an application claiming the benefit of Chinese patent application CN2020101855977 filed on Mar. 17, 2020., the contents of each of which are incorporated herein by reference in their entireties.

The present application claims the priority of Chinese patent application CN2020101855977 filed on Mar. 17, 2020. The contents of the above Chinese patent application are incorporated herein by reference in their entireties.

TECHNICAL FIELD

The present disclosure relates to a crystal form of aromatic vinyl derivatives, a preparation method therefor and a use thereof.

BACKGROUND

Human programmed death ligand 1 (PD-L1), also known as B7-H1, belongs to the B7 family member and is widely distributed in peripheral tissues and hematopoietic cells. The full-length cDNA of PD-L1q is 870 bp, encoding a type I transmembrane protein containing 290 amino acids, and PD-L1 is mainly expressed on the membrane surface of mature CD4T cells, CD8T cells, B cells, monocytes, dendritic cells (DCs), macrophages and other hematopoietic cells and some non-hematopoietic cells, such as expressed on the membrane surface of endothelial cells, islet cells, mast cells, etc. Among them, PD-L1 is highly expressed in various tumors, such as lung cancer, gastric cancer, multiple myeloma, melanoma and breast cancer, etc. Programmed death-1 (PD-1) is the main receptor of PD-L1, mainly distributed in immune-related cells such as T cells, B cells and NK cells and plays an important role in the immune response process of autoimmune diseases, tumors, infections, organ transplantation, allergies, immune privileges, etc.

PD-L1 inhibits the activation of T cells or induces apoptosis of mature T cells by interacting with its receptor PD-1, so that the immune response is suppressed. In the process of tumor development, cancer cells can induce T cell apoptosis by up-regulating the expression of PD-L1, so as to avoid its elimination by immune system. PD-L1 targeted antibody drugs can break the immune tolerance of tumor by specifically blocking the interaction between PD-1 and PD-L1, and restore the killing function of tumor-specific T cells to tumor cells, so as to realize tumor clearance.

PD-1/PD-L1 plays a negative immunoregulatory role. PD-1/PD-L1 signal can inhibit the activation and proliferation of T cells, and at the same time, the secretion of cytokines interleukin 2 (IL2), interferon γ and IL-10 also decreases (Eur. J. Immunol., 2002, 32(3), 634-643.). In addition, the immune function of PD-1/PD-L1 signal to B cells is similar to that of T cells, and when PD-1 is cross-linked with B cell antigen receptor, the cytoplasmic region of PD-1 reacts with tyrosinase containing protein tyrosinase 2 binding site, which finally blocks the activation of B cells. The role of immune negative regulatory molecule PD-1/PD-L1 in tumor immune escape has attracted more and more attention. A large number of studies have confirmed that PD-L1 on the surface of tumor cells in the tumor microenvironment is increased, and at the same time, PD-L1 binds to PD-1 on activated T cells and transmits negative regulatory signals, resulting in tumor antigen-specific T cells apoptosis or immune incompetence, thus inhibiting the immune response, and promoting the escape of tumor cells.

The currently marketed PD-1/PD-L1 antibody inhibitors include BMS' Nivolumab (2014), Merck's Lambrolizumab (2014), Junshi Bio's Toripalimab, Innovent's Sintilimab, Roche's Atezolizumab and AstraZeneca's Durvalumab. Compared with biological macromolecules, small molecular compounds can cross the cell membrane and act on intracellular targets, after chemical modification, small molecular compounds often have better bioavailability and compliance, are effectively prevented from decomposing and inactivating due to the digestion of enzymes in the intestinal tract.

At present, there is no small molecule PD-1/PD-L1 inhibitor which is convenient to use and effective for oral administration on the market, patent CN109988144A disclosed an aromatic ethylene PD-L1 small molecule compound with a chemical structural formula of

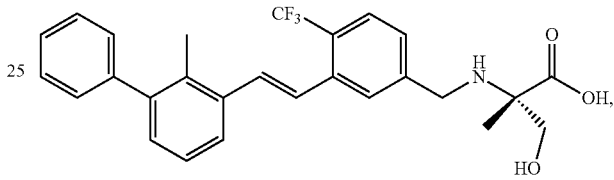

which had a strong inhibitory effect on the combination of PD-1 and PD-L1, restored the killing function of tumor-specific T cells to tumor cells, and could effectively alleviate and treat PD-1/PD-L1 related diseases such as cancer.

In addition to having a good inhibitory activity against kinases, the crystal structure of a pharmaceutically active ingredient often affects the chemical stability of drugs, and the differences in crystal form, preparation method and storage condition may lead to changes in the crystal structure of the compound, sometimes along with generation of crystal forms of other forms. Generally speaking, amorphous pharmaceutical products have no regular crystal structure, and often have other defects, such as poor product stability, fine crystal precipitation, easy caking, poor fluidity, etc., and these differences often lead to difficulties in production scale-up. At the same time, the crystal form has a crucial impact on the stability of the drug during production, processing, storage, transportation, and bioavailability during treatment, moreover, from the perspective of obtaining a commercially viable production method or from the perspective of producing pharmaceutical composition containing active compounds; chemical stability, solid state stability and storage duration of the active ingredient are all very important factors, thus providing a suitable form of the drug with the desired properties for drug production and storage is very important.

CONTENT OF THE PRESENT INVENTION

The present disclosure provides a crystal form of aromatic vinyl derivatives, a preparation method therefor and a use thereof. The crystal forms of the present disclosure have good stability, are less hygroscopic and are easy to prepare, and have an important value for drug optimization and development.

The present disclosure provides a crystal form A of a compound as shown in formula I, the X-ray powder diffraction pattern of the crystal form A represented by 2θ angles has characteristic peaks at 9.923±0.2°, 10.883±0.2° and 17.357±0.2°;

or, has characteristic peaks at 3.979±0.2°, 9.923±0.2°, 10.883±0.2°, 17.357±0.2°, 18.607±0.2° and 19.294±0.2°;

or, has characteristic peaks at 3.979±0.2°, 4.991±0.2°, 9.923±0.2°, 10.883±0.2°, 14.251±0.2°, 16.210±0.2°, 17.357±0.2°, 18.607±0.2°, 19.294±0.2°, 19.594±0.2° and 20.792±0.2°;

or, has characteristic peaks at 3.979±0.2°, 4.991±0.2°, 7.113±0.2°, 8.135±0.2°, 9.923±0.2°, 10.883±0.2°, 11.613±0.2°, 14.251±0.2°, 14.866±0.2°, 16.210±0.2°, 17.357±0.2°, 18.607±0.2°, 19.294±0.2°, 19.594±0.2°, 20.792±0.2°, 21.272±0.2°, 24.437±0.2°, 25.257±0.2°, 26.2295±0.2°, 27.870±0.2°, 28.631±0.2°, 29.126±0.2°, 29.943±0.2°;

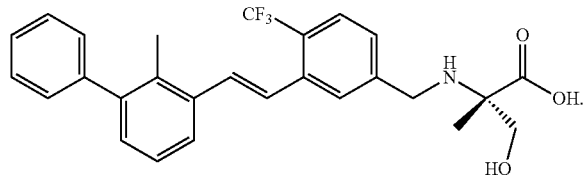

I

In some preferred embodiments of the present disclosure, in the X-ray powder diffraction pattern of the crystal form A represented by 2θ angles, the 2θ values are as shown in table 1:

TABLE 1

| 2θ (2θ ± 0.2°) | Relative intensity (%) |
|---|---|
| 3.979 | 25.2 |
| 4.991 | 14.3 |
| 7.113 | 1.5 |
| 8.135 | 1.5 |
| 9.923 | 36.3 |
| 10.883 | 27.0 |
| 11.613 | 6.6 |
| 14.251 | 13.2 |
| 14.866 | 4.4 |
| 16.210 | 18.0 |
| 17.357 | 100.0 |
| 18.607 | 25.0 |
| 19.294 | 26.3 |
| 19.594 | 11.4 |
| 20.792 | 11.2 |
| 21.272 | 6.8 |
| 24.437 | 6.7 |
| 25.257 | 5.9 |
| 26.229 | 4.4 |
| 27.870 | 3.7 |
| 28.631 | 1.9 |
| 29.126 | 5.2 |
| 29.943 | 1.5 |

In some preferred embodiments of the present disclosure, in the polarized light microscope analysis of the crystal form A, the shape of the crystal form is preferably granular or rod-shaped, and the particle size is preferably 10-100 μm; the polarized light microscope analysis of the crystal form A can be carried out under the following conditions: the microscope is preferably a microscope with 10× objective lens, and the microscope is preferably a microscope with crossed polarizer. The polarized light micrograph of the crystal form A is preferably as shown in FIG. 1.

In some preferred embodiments of the present disclosure, in the differential scanning calorimetry analysis of the crystal form A, the differential scanning calorimetry analysis of the crystal form A has a thermal absorption peak at 247° C., and the melting heat is preferably 118.0 J/g; the differential scanning calorimetry analysis of the crystal form A can be carried out under the following conditions: preferably carrying out in an unsealed aluminum tray, preferably carrying out in a nitrogen flow (e.g., a nitrogen flow at a flow rate of 50 mL/min), preferably equilibrating at 25° C., preferably heating at the heating rate of 10° C./min, preferably heating from 25° C. to 300° C. The differential scanning calorimetry (DSC) analysis pattern of the crystal form A is preferably as shown in FIG. 2.

In some preferred embodiments of the present disclosure, in the thermogravimetric analysis of the crystal form A, the sample has a weight loss of only 0.1447% from 26.76° C. to 119.97° C., and the "%" is the weight percentage; the thermogravimetric analysis of the crystal form A can be carried out under the following conditions: preferably carrying out in a platinum sample tray, preferably carrying out in a nitrogen flow (e.g., a nitrogen flow at a flow rate of 60 mL/min), preferably heating at the heating rate of 10° C./min, preferably heating from 25° C. to 300° C. The thermogravimetric analysis (TGA) pattern of the crystal form A is preferably as shown in FIG. 3.

In some preferred embodiments of the present disclosure, in the X-ray powder diffraction analysis of the crystal form A, the X-ray powder diffraction analysis of the crystal form A can be carried out under the following conditions: preferably carrying out in the light source of CuK, preferably the X-ray intensity is 40 KV/40 mA, preferably the scanning mode is Theta-Theta, preferably the angle range is 2° to 40° (for example, 4° to 40°), preferably the step size is 0.05°, and preferably the scanning speed is 0.5 second/step. The X-ray powder diffraction (XRPD) pattern of the crystal form A is preferably as shown in FIG. 4.

In some preferred embodiments of the present disclosure, in the dynamic vapor sorption analysis of crystal form A, the hygroscopic weight gain is 0.310% at 80% RH and the hygroscopic weight gain is 0.409% at 95% RH, indicating that the crystal form A is slightly hygroscopic; the dynamic vapor sorption analysis of crystal form A can be carried out under the following conditions: preferably carrying out at 25° C., preferably carrying out at 0% RH after drying for 60 min. The dynamic vapor sorption (DVS) analysis pattern of the crystal form A is preferably as shown in FIG. 5.

The present disclosure provides a crystal form B of the compound as shown in formula I, the X-ray powder diffraction pattern of the crystal form B represented by 2θ angles has characteristic peaks at 3.424±0.2°, 6.576±0.2° and 19.297±0.2°;

or, has characteristic peaks at 3.424±0.2°, 6.576±0.2°, 18.217±0.2°, 19.297±0.2°, 20.901±0.2° and 26.379±0.2°;

or, has characteristic peaks at 3.424±0.2°, 6.576±0.2°, 14.467±0.2°, 16.406±0.2°, 17.567±0.2°, 18.217±0.2°, 19.297±0.2°, 20.557±0.2°, 20.901±0.2°, 22.460±0.2°, 25.084±0.2°, 25.878±0.2°, 26.379±0.2° and 28.983±0.2°;

or, has characteristic peaks at 3.424±0.2°, 6.576±0.2°, 9.732±0.2°, 11.304±0.2°, 12.905±0.2°, 13.918±0.2°, 14.467±0.2°, 16.406±0.2°, 17.567±0.2°, 18.217±0.2°, 19.297±0.2°, 20.557±0.2°, 20.901±0.2°, 22.460±0.2°, 23.872±0.2°, 25.084±0.2°, 25.878±0.2°, 26.379±0.2°, 28.983±0.2°, 29.531±0.2°, 30.459±0.2°, 32.171±0.2°, 34.297±0.2°, 37.676±0.2° and 38.902±0.2°;

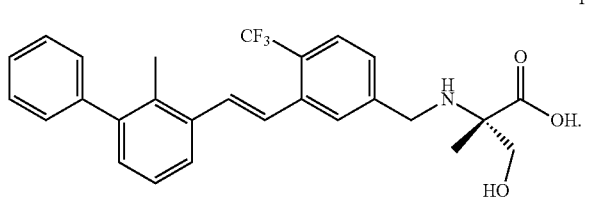

In some preferred embodiments of the present disclosure, in the X-ray powder diffraction pattern of the crystal form B represented by 2θ angles, the 2θ values are as shown in table 2:

TABLE 2

| 2θ (2θ ± 0.2°) | Relative intensity (%) |
| --- | --- |
| 3.424 | 89.1 |
| 6.576 | 100.0 |
| 9.732 | 3.4 |
| 11.304 | 3.7 |
| 12.905 | 3.2 |
| 13.918 | 8.7 |
| 14.467 | 13.9 |
| 16.406 | 17.6 |
| 17.567 | 11.6 |
| 18.217 | 26.6 |
| 19.297 | 87.8 |
| 20.557 | 16.2 |
| 20.901 | 35.7 |
| 22.460 | 24.7 |
| 23.872 | 8.3 |
| 25.084 | 12.1 |
| 25.878 | 20.0 |
| 26.379 | 25.5 |
| 28.983 | 10.2 |
| 29.531 | 8.0 |
| 30.459 | 1.6 |
| 32.171 | 2.3 |
| 34.297 | 2.0 |
| 37.676 | 1.9 |
| 38.902 | 1.6 |

In some preferred embodiments of the present disclosure, in the X-ray powder diffraction analysis of the crystal form B, the X-ray powder diffraction analysis of the crystal form B can be carried out under the following conditions: preferably carrying out in the light source of CuK, preferably the X-ray intensity is 40 KV/40 mA, preferably the scanning mode is Theta-Theta, preferably the angle range is 2° to 40° (for example, 4° to 40°), preferably the step size is 0.05°, and preferably the scanning speed is 0.5 second/step. The X-ray powder diffraction (XRPD) pattern of the crystal form B is preferably as shown in FIG. 6.

In some preferred embodiments of the present disclosure, in the differential scanning calorimetry analysis of the crystal form B, the differential scanning calorimetry analysis of the crystal form B has a thermal absorption peak at 243° C., and the melting heat is preferably 93.73 J/g; the differential scanning calorimetry analysis of the crystal form B can be carried out under the following conditions: preferably carrying out in an unsealed aluminum tray, preferably carrying out in a nitrogen flow (e.g., a nitrogen flow at a flow rate of 50 mL/min), preferably equilibrating at 25° C., preferably heating at the heating rate of 10° C./min, prefer- ably heating from 25° C. to 300° C. The differential scanning calorimetry (DSC) analysis pattern of the crystal form B is preferably as shown in FIG. 7.

In some preferred embodiments of the present disclosure, in the thermogravimetric analysis of the crystal form B, the sample has a weight loss of 5.2% from 25.3° C. to 92.5° C., and the "%" is the weight percentage; the thermogravimetric analysis of the crystal form B can be carried out under the following conditions: preferably carrying out in a platinum sample tray, preferably carrying out in a nitrogen flow (e.g., a nitrogen flow at a flow rate of 60 mL/min), preferably heating at the heating rate of 10° C./min, preferably heating from 25° C. to 300° C. The thermogravimetric analysis (TGA) pattern of the crystal form B is preferably as shown in FIG. 8.

In some preferred embodiments of the present disclosure, in the dynamic vapor sorption analysis of crystal form B, the sample has a weight gain of 7.235% from 0% to 95% relative humidity (RH), indicating that the crystal form B is hygroscopic; the dynamic vapor sorption analysis of crystal form B can be carried out under the following conditions: preferably carrying out at 25° C., preferably carrying out at 0% RH after drying for 60 min. The dynamic vapor sorption (DVS) analysis pattern of the crystal form B is preferably as shown in FIG. 9.

The present disclosure provides a crystal form C of the compound as shown in formula I, the X-ray powder diffraction pattern of the crystal form C represented by 2θ angles has characteristic peaks at 6.250±0.2°, 18.458±0.2° and 19.302±0.2°;

or, has characteristic peaks at 6.250±0.2°, 8.779±0.2°, 13.720±0.2°, 18.458±0.2° and 19.302±0.2°;

or, has characteristic peaks at 6.250±0.2°, 8.779±0.2°, 12.635±0.2°, 13.720±0.2°, 16.525±0.2°, 18.458±0.2° and 19.302±0.2°;

or, has characteristic peaks at 6.250±0.2°, 6.979±0.2°, 8.779±0.2°, 12.635±0.2°, 13.720±0.2°, 16.525±0.2°, 18.458±0.2°, 19.302±0.2°, 20.852±0.2°, 22.345±0.2°, 24.772±0.2°, 25.230±0.2° and 27.285±0.2°;

or, has characteristic peaks at 6.250±0.2°, 6.979±0.2°, 8.779±0.2°, 12.635±0.2°, 13.720±0.2°, 15.285±0.2°, 16.525±0.2°, 18.458±0.2°, 19.302±0.2°, 20.852±0.2°, 22.345±0.2°, 24.772±0.2°, 25.230±0.2°, 25.996±0.2°, 27.285±0.2°, 28.303±0.2°, 28.829±0.2°, 29.699±0.2°, 30.703±0.2°, 33.133±0.2°, 34.655±0.2°, 36.829±0.2°, 37.967±0.2°;

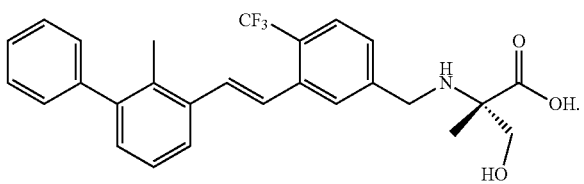 [SMILES: Cc1c(/C=C/c2cc(CN[C@@](C)(CO)C(=O)O)ccc2C(F)(F)F)cccc1-c1ccccc1]

In some preferred embodiments of the present disclosure, in the X-ray powder diffraction pattern of the crystal form C represented by 2θ angles, the 2θ values are as shown in table 3:

TABLE 3

| 2θ (2θ ± 0.2°) | Relative intensity (%) |
| --- | --- |
| 6.250 | 100 |
| 6.979 | 15.3 |
| 8.779 | 38.6 |
| 12.635 | 21.3 |
| 13.720 | 32.6 |
| 15.285 | 3.1 |
| 16.525 | 24.1 |
| 17.696 | 5.5 |
| 18.458 | 73.0 |
| 19.302 | 59.0 |
| 20.852 | 15.4 |
| 22.345 | 19.1 |
| 24.772 | 14.3 |
| 25.230 | 11.5 |
| 25.996 | 4.1 |
| 27.285 | 13.2 |
| 28.303 | 4.1 |
| 28.829 | 3.7 |
| 29.699 | 2.3 |
| 30.703 | 5.6 |
| 33.133 | 3.1 |
| 34.655 | 1.9 |
| 36.829 | 2.4 |
| 37.967 | 3.1 |

In some preferred embodiments of the present disclosure, in the X-ray powder diffraction analysis of the crystal form C, the X-ray powder diffraction (XRPD) pattern of the crystal form C is preferably as shown in FIG. 10.

In some preferred embodiments of the present disclosure, in the differential scanning calorimetry analysis of the crystal form C, the differential scanning calorimetry analysis of the crystal form C has a thermal absorption peak at 243° C., and the melting heat is preferably 99.33 J/g; the differential scanning calorimetry analysis of the crystal form C can be carried out under the following conditions: preferably carrying out in an unsealed aluminum tray, preferably carrying out in a nitrogen flow (e.g., a nitrogen flow at a flow rate of 50 mL/min), preferably equilibrating at 25° C., preferably heating at the heating rate of 10° C./min, preferably heating from 25° C. to 300° C. The differential scanning calorimetry (DSC) analysis pattern of the crystal form C is preferably as shown in FIG. 11.

In some preferred embodiments of the present disclosure, in the thermogravimetric analysis of the crystal form C, the sample has a weight loss of 0.62% from 24.0° C. to 58.0° C., and the sample has a weight loss of 2.5% from 58.0° C. to 162.3° C., and the "%" is the weight percentage; the thermogravimetric analysis of the crystal form C can be carried out under the following conditions: preferably carrying out in a platinum sample tray, preferably carrying out in a nitrogen flow (e.g., a nitrogen flow at a flow rate of 60 mL/min), preferably heating at the heating rate of 10° C./min, preferably heating from 25° C. to 300° C. The thermogravimetric analysis (TGA) pattern of the crystal form C is preferably as shown in FIG. 12.

In some preferred embodiments of the present disclosure, in the dynamic vapor sorption analysis of crystal form C, the sample has a weight gain of 4.767% from 0% RH to 95% RH, indicating that the crystal form C is hygroscopic; the dynamic vapor sorption analysis of crystal form C can be carried out under the following conditions: preferably carrying out at 25° C., preferably carrying out at 0% RH after drying for 60 min. The dynamic vapor sorption (DVS) analysis pattern of the crystal form C is preferably as shown in FIG. 13.

In the present disclosure, the ray used in the X-ray powder diffraction is Kα ray.

In the present disclosure, the target type used in the X-ray powder diffraction is a Cu target.

The present disclosure also provides a method of preparing the crystal form A of the compound as shown in formula I, comprising the following steps: in a solvent, crystallizing the compound as shown in formula I; the crystallization method is suspension equilibrium method, solution heating-slow cooling method or anti-solvent method; the solvent is ethanol, and when the crystallization method is anti-solvent method, the anti-solvent is an alkane solvent.

In the method of preparing the crystal form A, when the crystallization method is anti-solvent method, the alkane solvent can be a conventional alkane solvent in the art, and the alkane solvent is preferably $C_{1-10}$ alkane solvent, more preferably n-heptane.

In the method of preparing the crystal form A, the crystallization temperature can be a conventional crystallization temperature in the art, and the crystallization temperature is preferably 20° C. to 60° C. (for example, room temperature (20° C. to 25° C.) or 50° C.).

In the method of preparing the crystal form A, the mass-volume ratio of the compound as shown in formula I to the solvent can be a conventional ratio in the art, preferably 5 mg/mL to 20 mg/mL (for example, 7.7 mg/mL to 20 mg/mL).

In the method of preparing the crystal form A, the crystallization time is not particularly limited, as long as the crystals can be precipitated, and the crystallization time is preferably 1 hour to 20 days (for example, 1 hour to 2 hours, 5 hours to 6 hours or 10 days to 20 days).

In the method of preparing the crystal form A, when the crystallization method is anti-solvent method, the mass ratio of the anti-solvent to the solvent can be a conventional ratio in the art, preferably 5:1 to 8:1 (for example, 6.5:1).

In the method of preparing the crystal form A, which preferably comprises the following steps: mixing the solvent with the compound as shown in formula I, sonicating, rotating and centrifuging to obtain the target crystal form. The rotating is preferably carried out under shade. The rotating is preferably carried out at room temperature. The rotating is preferably carried out on a Labquaker rotator. The rotating is preferably carried out for 10 days to 20 days. After the centrifuging is completed, the operation of drying is also preferably comprised. The mass-volume ratio of the compound as shown in formula I to the solvent is preferably 5 mg/mL to 20 mg/mL (for example, 7.7 mg/mL to 20 mg/mL).

In the method of preparing the crystal form A, which preferably comprises the following steps: mixing the solvent with the compound as shown in formula I, heating and dissolving, slowly cooling to room temperature and centrifuging to obtain the target crystal form. The temperature for heating and dissolving is preferably 50° C. to 60° C. The heating and dissolving are preferably heating in a water bath. The heating and dissolving preferably comprise a stirring operation at the same time, and the stirring speed is preferably 200 rpm. After the heating and dissolving are completed, the operation of heat preservation is preferably comprised, and the heat preservation time is preferably 15 min. After the heating and dissolving are completed, the operation of filtering while hot is also preferably comprised, and the filtering preferably adopts a 0.45 μm filter membrane. The rate of slow cooling is preferably 6° C./h. After the centrifuging is completed, the operation of evaporating the solvent to dryness is also preferably comprised. The mass-volume ratio of the compound as shown in formula I to the solvent is preferably 5 mg/mL to 20 mg/mL (for example, 7.7 mg/mL to 20 mg/mL).

In the method of preparing the crystal form A, which preferably comprises the following steps: mixing the solvent with the compound as shown in formula I, heating and dissolving, adding the anti-solvent dropwise, then naturally cooling and centrifuging to obtain the target crystal form. The temperature for heating and dissolving is preferably 50° C. to 60° C. The heating and dissolving preferably comprise a stirring operation at the same time, and the stirring speed is preferably 200 rpm. After the heating and dissolving are completed, the operation of heat preservation is preferably comprised, and the heat preservation time is preferably 15 min. After the heating and dissolving are completed, the operation of filtering while hot is preferably also comprised, and the filtering preferably adopts a 0.45 µm filter membrane. The adding the anti-solvent dropwise preferably comprises the operation of stirring at the same time. The volume ratio of the anti-solvent to the solvent is preferably 5:1 to 8:1 (for example, 6.5:1). After the adding the anti-solvent dropwise is completed, the operation of heat preservation is preferably comprised, and the heat preservation time is preferably 10 min. After the centrifuging is completed, the operation of evaporating the solvent to dryness is also preferably comprised. The mass-volume ratio of the compound as shown in formula I to the solvent is preferably 5 mg/mL to 20 mg/mL (for example, 7.7 mg/mL to 20 mg/mL).

The present disclosure also provides a method of preparing the crystal form B of the compound as shown in formula I, comprising the following steps: in a solvent, crystallizing the compound as shown in formula I; the crystallization method is suspension equilibrium method or anti-solvent method; when the crystallization method is suspension equilibrium method, the solvent is water, or ethanol and water; and when the crystallization method is anti-solvent method, the solvent is ethanol or tetrahydrofuran, and the anti-solvent is water.

In the method of preparing the crystal form B, the water can be one or more of distilled water, deionized water, purified water, tap water and mineral water.

In the method of preparing the crystal form B, the crystallization temperature can be a conventional temperature in the art, and the crystallization temperature is preferably 20° C. to 60° C. (for example, room temperature (20° C. to 25° C.) or 50° C.).

In the method of preparing the crystal form B, the mass-volume ratio of the compound as shown in formula I to the solvent can be a conventional ratio in the art, preferably 5 mg/mL to 40 mg/mL (for example, 7.7 mg/mL, 11.1 mg/mL, 20 mg/mL or 33.3 mg/mL).

In the method of preparing the crystal form B, when the crystallization method is suspension equilibrium method, and when the solvent is ethanol and water, the volume ratio of ethanol to water is preferably 1:3 to 1:5 (for example, 1:4).

In the method of preparing the crystal form B, when the crystallization method is anti-solvent method, the volume ratio of the anti-solvent to the solvent is preferably 1:1 to 4:1 (for example, 1:1 or 2.7:1).

In the method of preparing the crystal form B, the crystallization time is not particularly limited, as long as the crystals can be precipitated, and the crystallization time is preferably 1 hour to 20 days (for example, 1 hour to 2 hours, 1 day or 17 days).

In the method of preparing the crystal form B, when the crystallization method is suspension equilibrium method, the method of preparing the crystal form B comprises the following steps: mixing the solvent with the compound as shown in formula I, slurrying, and separating the solid to obtain the target crystal form. The slurrying is preferably carried out at room temperature. The slurrying is preferably carried out under stirring. The stirring is preferably magnetic stirring. The slurrying is preferably carried out for 1 day to 17 days. The separating the solid is preferably centrifuging or filtering. After the separating the solid is completed, the operation of drying is also preferably comprised, and the drying is preferably carried out at 40° C., and the drying is preferably carried out for 4 hours. The mass-volume ratio of the compound as shown in formula I to the solvent is preferably 5 mg/mL to 40 mg/mL (for example, 7.7 mg/mL, 11.1 mg/mL, 20 mg/mL or 33.3 mg/mL).

In the method of preparing the crystal form B, when the crystallization method is anti-solvent method, the method of preparing the crystal form B comprises the following steps: mixing the solvent with the compound as shown in formula I, heating and dissolving, adding the anti-solvent dropwise, then naturally cooling and centrifuging to obtain the target crystal form. The temperature for heating and dissolving is preferably 50° C. to 60° C. The heating and dissolving preferably comprise a stirring operation at the same time, and the stirring speed is preferably 200 rpm. After the heating and dissolving are completed, the operation of heat preservation is preferably comprised, and the heat preservation time is preferably 15 min. After the heating and dissolving are completed, the operation of filtering while hot is preferably comprised, and the filtering preferably adopts a 0.45 µm filter membrane. The adding the anti-solvent dropwise is preferably adding while stirring. After the adding the anti-solvent dropwise is completed, the operation of heat preservation is preferably comprised, and the heat preservation time is preferably 10 min. After the centrifuging is completed, the operation of evaporating the solvent to dryness is preferably also comprised. The mass-volume ratio of the compound as shown in formula I to the solvent is preferably 5 mg/mL to 40 mg/mL (for example, 7.7 mg/mL, 11.1 mg/mL, 20 mg/mL or 33.3 mg/mL).

The present disclosure also provides a method of preparing the crystal form C of the compound as shown in formula I, comprising the following steps: in a solvent, crystallizing the compound as shown in formula I by suspension equilibrium method; the solvent is isopropanol, N,N-dimethylacetamide, or acetone and water.

In the method of preparing the crystal form C, when the solvent is acetone and water, the volume ratio of acetone to water is preferably 7:1 to 10:1 (for example, 8:1).

In the method of preparing the crystal form C, the water can be one or more of distilled water, deionized water, purified water, tap water and mineral water.

In the method of preparing the crystal form C, the crystallization temperature can be a conventional temperature in the art, and the crystallization temperature is preferably room temperature.

In the method of preparing the crystal form C, the mass-volume ratio of the compound as shown in formula I to the solvent can be a conventional ratio in the art, the mass-volume ratio of the compound as shown in formula I to the solvent is preferably 10 mg/mL to 50 mg/mL (for example, 20 mg/mL, 40 mg/mL or 44.4 mg/mL).

In the method of preparing the crystal form C, the crystallization time is not particularly limited, as long as the crystals can be precipitated, and the crystallization time is preferably 1 day to 20 days (for example, 1 day, 7 days, 10 days or 20 days).

In the method of preparing the crystal form C, which comprises the following steps: mixing the solvent with the compound as shown in formula I, slurrying or rotating, separating the solid to obtain the target crystal form. After the mixing is completed, the operation of sonicating is also preferably comprised, and the sonicating is preferably carried out for 1 min. When the method of preparing the crystal form C comprises slurrying, the slurrying is preferably carried out for 1 day, and the slurrying is preferably carried out under stirring, and the stirring is preferably magnetic stirring. When the method of preparing the crystal form C comprises rotating, the rotating is preferably carried out for 10 to 20 days, and the rotating is preferably carried out on a Labquaker rotator, and the rotating is preferably carried out under shade. The separating the solid is preferably centrifuging or filtering. After the separating the solid is completed, the operation of the drying is also preferably comprised. The drying is preferably carried out at 70° C., and the drying is preferably carried out for 4 hours. The mass-volume ratio of the compound as shown in formula I to the solvent is preferably 10 mg/mL to 50 mg/mL (for example, 20 mg/mL, 40 mg/mL or 44.4 mg/mL).

The present disclosure also provides a use of the crystal forms of the compound as shown in formula I in the manufacture of a medicament. Use of the compound in a medicament for preventing, relieving and/or treating related diseases caused by cancer; the cancer is preferably one or more of lung cancer, esophageal cancer, gastric cancer, colorectal cancer, liver cancer, nasopharyngeal cancer, brain tumor, breast cancer, cervical cancer, blood cancer and bone cancer. The medicament preferably comprises a therapeutically effective amount of the crystal form A, B or C of the compound as shown in formula I.

As used herein, the term "d" refers to day, the term "h" refers to hour, and the term "min" refers to minute.

On the basis of conforming to the common sense in the art, the above preferred conditions can be arbitrarily combined to obtain the preferred examples of the present disclosure.

The reagents and raw materials used in the present disclosure are commercially available.

The positive progressive effect of the present disclosure is as follows:

1. The crystal form of the compound as shown in formula I has not been recorded in the prior art, and many new crystal forms of the compound have been found in the present disclosure for the first time. Through extensive experiments and screening, crystal form A, crystal form B and crystal form C are selected as candidates.

2. The crystal form A, crystal form B and crystal form C prepared by the present disclosure have a good stability, are less hygroscopic, and are easy to prepare, can avoid the risk of crystal transformation during drug development or production process, avoid changes in bioavailability and efficacy, can be developed into a dosage form suitable for clinical use, which has a strong economic value.

The present disclosure also provides a method of preparing a new crystal form of the compound as shown in formula I, the method is easy to operate and has a high reproducibility, and the solvent is not easy to remain, and the method is environmentally friendly, and suitable for different large-scale production.

DETAILED DESCRIPTION OF THE PREFERRED EMBODIMENT

Figure 1:
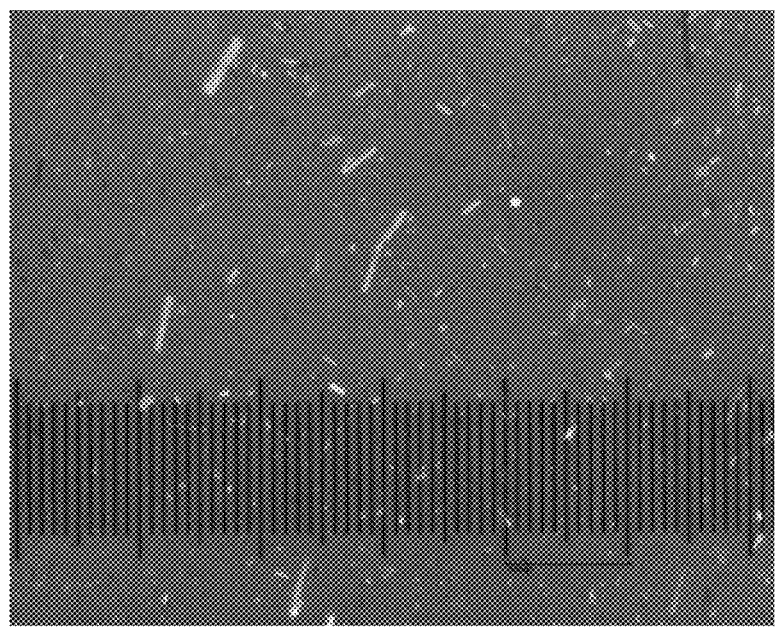
FIG. 1 is the polarized light micrograph of the crystal form A of the compound as shown in formula I.

The present disclosure is further described below by way of embodiments, but the present disclosure is not thereby limited to the scope of the described embodiments. The experimental methods not specified in the specific conditions in the following embodiments are selected according to the conventional methods and conditions, or according to the commodity instructions.

In the preparation method of the following crystal forms, the volume (mL) of the added solvent=sample mass×volume multiple (mL), for example, the volume of ethanol in the preparation method I of embodiment 1 is: 0.02×50 mL=1 mL.

Preparation of Amorphous Compound I (the Compound as Shown in Formula I):

At room temperature, glacial acetic acid (32.8 mg, 0.54 mmol) was added to a mixed solution of compound 5-a (preparation of compound 5-a was obtained according to the method in patent CN109988144A) and (S)-2-methylserine (65 mg, 0.54 mmol) in methanol (10 mL) and dichloromethane (10 mL), and the reaction solution was stirred at room temperature for 1 hour. Then, sodium cyanoborohydride (85.8 mg, 1.36 mmol) was added thereto and the mixture was stirred for 16 hours. The reaction solution was concentrated under reduced pressure, and the residue was dissolved in ethyl acetate (50 mL), washed with water (20 mL) and saturated brine (20 mL), and then the organic phase was dried over anhydrous sodium sulfate, concentrated under reduced pressure. The residue was separated by silica gel thin layer chromatography preparative plate with the mobile phase of dichloromethane:methanol=10:1, and the silica gel mixed with compound I was washed with methanol (20 mL×3), and the washing solution was concentrated under reduced pressure to obtain amorphous compound I (24 mg, yield: 18.7%). LC-MS (ESI): m/z=468 [M-H]$^-$ $^1$H NMR (500 MHz, CD$_3$OD)δ: 8.17 (s, 1H), 7.81-7.79 (d, J=8.5 Hz, 1H), 7.68-7.62 (m, 2H), 7.57-7.55 (d, J=8.0 Hz, 1H), 7.46-7.43 (m, 2H), 7.39-7.28 (m, 5H), 7.20-7.19 (d, J=7.0 Hz, 1H), 4.36-4.28 (q,2H), 4.03-4.00 (d, J=12.5 Hz, 1H), 3.86-3.84 (d, J=12.5 Hz, 1H), 2.33 (s,3H), 1.57 (s,3H) ppm.

Embodiment 1: A Method of Preparing the Crystal Form A

Preparation method I: 20 mg of the compound as shown in formula I was weighed and added to a 4 mL glass bottle, and 50 times the volume of ethanol (EtOH) was added to the glass bottle, then the mixture was sonicated for 1 minute to obtain a suspension of the sample, and the suspension sample bottle was wrapped with an aluminum foil to shading and placed on a Labquaker rotator, and the mixture was equilibrated at room temperature (about 20 to 25° C.) with 360° rotation, and samples were taken at 10 days and 20 days, respectively, centrifuged, and characterized by XRPD after drying, the results were characterized as crystal form A.

Preparation method II: 20 mg of the compound as shown in formula I was weighed and added to a 10 mL glass bottle, then 130 times the volume of ethanol (EtOH) was added to the glass bottle; the sample was placed on a magnetic heating stirrer, and the water bath temperature was about 50° C., and the rotation speed was 200 rpm. The sample was heated to accelerate the dissolution, and the heat preservation was carried out for 15 min, and the solution was filtered while hot with a 0.45 µm filter membrane. The filtrate was transferred to a new glass bottle, and slowly cooled down to room temperature (20 to 25° C.) at a rate of 6° C./h. The solvent system of the precipitated solid was centrifuged and the solid was taken out, and after the solvent was evaporated to dryness, then the solid was characterized by XRPD, and the results were characterized as crystal form A.

Preparation method III (anti-solvent method): About 80 mg of the compound as shown in formula I sample was weighed and added to a 20 mL glass bottle, then 130 times the volume of good solvent ethanol (EtOH) was added to the bottle. The sample was placed on a magnetic heating stirrer, and the water bath temperature was about 50° C., and the rotation speed was 200 rpm. The sample was heated to accelerate the dissolution, and the heat preservation was carried out for 15 min, and the solution was filtered while hot with a 0.45 µm filter membrane. The filtrate was transferred to a new bottle, and 850 times the volume of the anti-solvent n-heptane was slowly added dropwise to each bottle under stirring, and the heat preservation was carried out for 10 min, then naturally cooled down. The solvent system of the precipitated solid was centrifuged and the solid was taken out, and after the solvent was evaporated to dryness, then the solid was characterized by XRPD, and the results were characterized as crystal form A.

Embodiment 2: A Method of Preparing the Crystal Form B

Preparation method I: 200 mg of the compound as shown in formula I was weighed and added to a bottle, then 10 times the volume of ethanol and 40 times the volume of water were added to the bottle, and the mixture was magnetic stirred and slurried for one day at room temperature. The solution was centrifuged, and the solid was collected, and dried at 40° C. for 4 hours; the solid after drying was characterized, and the results were characterized as crystal form B.

Preparation method II: 100 mg of the compound as shown in formula I was weighed and added to a glass bottle, then 30 times the volume of water was added to the glass bottle, and the mixture was magnetic stirred and slurried for 17 days at room temperature. The solution was filtered under reduced pressure, and dried at 40° C. for 4 hours, and then the solid was characterized by XRPD, and the results were characterized as crystal form B.

Preparation method III (anti-solvent method): About 80 mg of the compound as shown in formula I sample was respectively weighed and added to a 20 mL glass bottle. According to the following table, an appropriate volume of good solvent (see table 4 for specific volume) was respectively added to the bottle; the sample bottle was placed on a magnetic heating stirrer, and the water bath temperature was about 50° C., and the rotation speed was 200 rpm. The temperature in the water bath was maintained to promote sample dissolution, and the heat preservation was carried out for 15 min, and the solution was filtered while hot with a 0.45 µm filter membrane. The filtrate was transferred to a new bottle, and different anti-solvents were slowly added dropwise to each bottle in turn under stirring, and the heat preservation was carried out for 10 min, then the mixture was naturally cooled down. The solvent system of the precipitated solid was centrifuged and the solid was taken out, and after the solvent was evaporated to dryness, then the solid was characterized by XRPD, and the results were characterized as crystal form B.

TABLE 4

| Number | Good solvent/ anti-solvent | Volume multiple | Remark | Crystal form |
| --- | --- | --- | --- | --- |
| 1 | Ethanol/water | 130/130 | Magnetic stirring at room temperature for 8 days | Crystal form B |
| 2 | Tetrahydrofuran/water | 90/245 | Magnetic stirring at room temperature for 7 days | Crystal form B |

Embodiment 3: A Method of Preparing the Crystal Form C

Preparation method I: 200 mg of the compound as shown in formula I sample was weighed, then 20 times the volume of acetone and 2.5 times the volume of water were added thereto. The mixture was magnetic stirred and slurried for one day at room temperature, and then the solution was centrifuged, and the solid was collected, and dried at 70° C. for 4 hours. The solid after drying was characterized by XRPD, and the results were characterized as crystal form C.

Preparation method II: 200 mg of the compound as shown in formula I and 25 times the volume of isopropanol (IPA) were magnetic stirred and slurried for 7 days at room temperature, filtered under reduced pressure, and the solid was dried at 70° C. for 4 hours, and then the solid sample was characterized by XRPD, and the results were characterized as crystal form C.

Preparation method III: 20 mg of the compound as shown in formula I was weighed and added to a 4 mL glass bottle, and 50 times of the volume of N,N-dimethylacetamide (DMA) was added to the glass bottle, then the mixture was sonicated for 1 minute to obtain a suspension of the sample, and the suspension sample bottle was wrapped with an aluminum foil to shading and placed on a Labquaker rotator, and the mixture was equilibrated at room temperature (about 20 to 25° C.) with 360° rotation, and samples were taken at 10 days and 20 days, respectively, centrifuged, and characterized by XRPD after drying, the results were characterized as crystal form C.

The crystal forms A, B and C of the compound were subjected to structure determination, crystal form study and the like by X-ray powder diffraction (XRPD) pattern, differential scanning calorimetry (DSC) analysis, thermogravimetric analysis (TGA) or dynamic vapor sorption (DVS), etc.

Embodiment 4: Characterization of Crystal Form A by Polarized Light Microscope (as Shown in FIG. 1)

A small amount of the crystal form A sample of the compound as shown in formula I was taken and placed on a glass slide with a scale, and an appropriate amount of liquid paraffin was added to disperse, covered with a cover glass, and placed under a microscope with a 10-fold objective lens to observe the shape and size of the particles and crystal form properties. The birefringence properties and crystal habit of the samples were displayed using crossed polarizers and photographed with a digital camera.

The results showed that the sample had obvious birefringence phenomenon under the polarized light microscope, and the sample was granular and rod-shaped, and the particle size was 10 to 100 μm.

Figure 2:
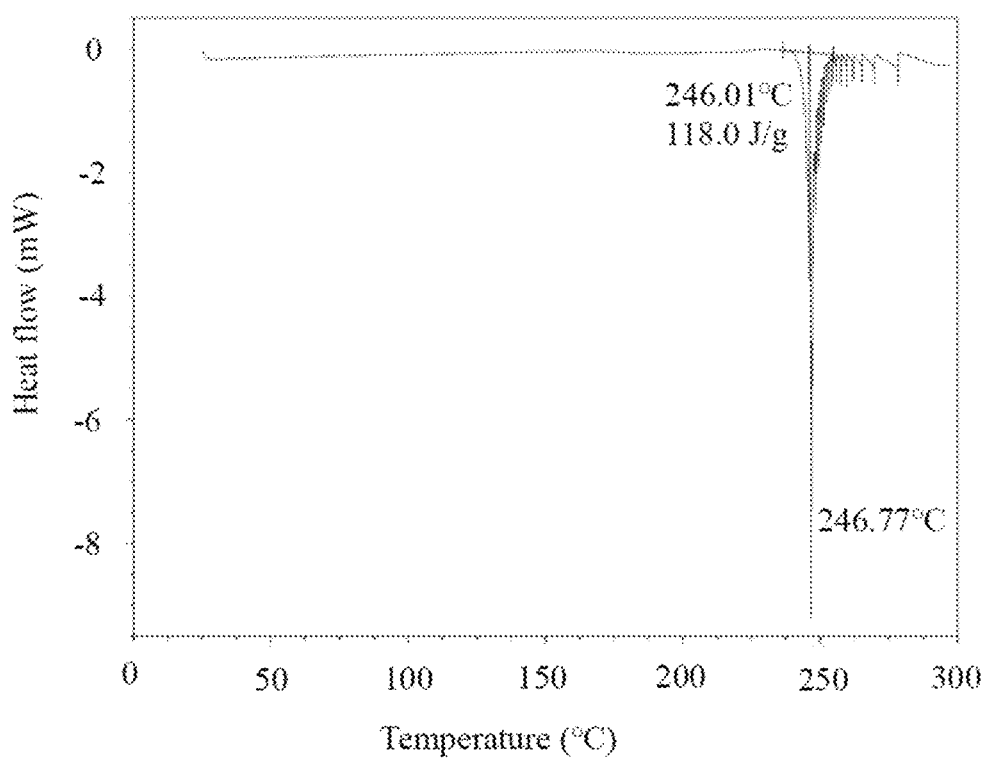
FIG. 2 is the DSC pattern of the crystal form A of the compound as shown in formula I.

Embodiment 5: Differential Scanning Calorimetry (DSC) Analysis of the Crystal Form a (as Shown in FIG. 2)

3.1820 mg of the crystal form A sample of the compound as shown in formula I was weighed, and placed in an unsealed aluminum tray; the sample was equilibrated at 25° C. in a nitrogen flow (50 mL/min), and then heated from 25° C. to 300° C. at a heating rate of 10° C./min, the results are detailed in table 5.

TABLE 5

| Sample | Initial temperature (° C.) | Maximum temperature (° C.) | Peak area (J/g) |
|---|---|---|---|
| Crystal form A | 246.01 | 246.77 | 118.0 |

Figure 3:
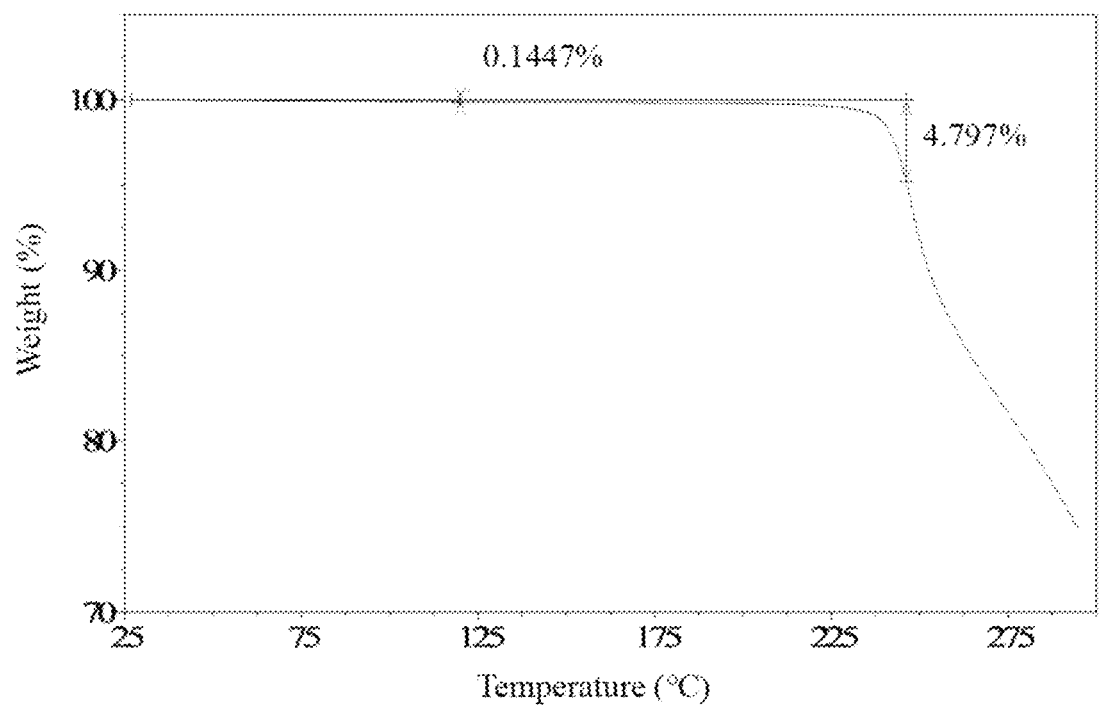
FIG. 3 is the TGA pattern of the crystal form A of the compound as shown in formula I.

Embodiment 6: Thermogravimetric Analysis (TGA) of the Crystal Form a (as Shown in FIG. 3)

15.3240 mg of the crystal form A sample of the compound as shown in formula I was weighed, and placed in a platinum sample tray; in a nitrogen flow (60 mL/min), the sample was heated from 25° C. to 300° C. at a heating rate of 10° C./min, and the sample was heated from 26.76° C. to 119.97° C., and the weight loss was only 0.1447%, indicating that the sample was almost free of water or solvent, the results are detailed in table 6.

TABLE 6

| Sample | Initial temperature (° C.) | End temperature (° C.) | Weight loss (%) |
|---|---|---|---|
| Crystal form A | 26.76 | 119.97 | 0.1447 |
|  | 26.76 | 246.16 | 4.797 |

Figure 4:
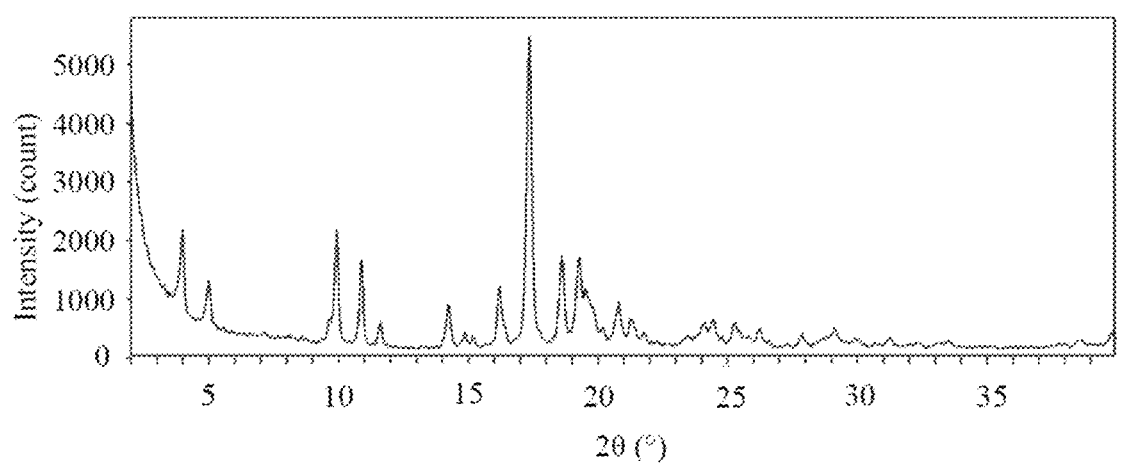
FIG. 4 is the XRPD pattern of the crystal form A of the compound as shown in formula I.

Embodiment 7: X-ray Powder Diffraction (XRPD) Analysis of the Crystal Form A (as Shown in FIG. 4)

The light source was CuK, the X-ray intensity was 40 KV/40 mA, the scanning mode was Theta-Theta, the scanning angle range was 4° to 40°, the step size was 0.05°, and the scanning speed was 0.5 second/step, and the results are detailed in table 7.

TABLE 7

| Number | 2θ (2θ ± 0.2°) | Relative intensity (%) |
|---|---|---|
| 1 | 3.979 | 25.2 |
| 2 | 4.991 | 14.3 |
| 3 | 7.113 | 1.5 |
| 4 | 8.135 | 1.5 |
| 5 | 9.923 | 36.3 |
| 6 | 10.883 | 27.0 |
| 7 | 11.613 | 6.6 |
| 8 | 14.251 | 13.2 |
| 9 | 14.866 | 4.4 |
| 10 | 16.210 | 18.0 |
| 11 | 17.357 | 100.0 |
| 12 | 18.607 | 25.0 |
| 13 | 19.294 | 26.3 |
| 14 | 19.594 | 11.4 |
| 15 | 20.792 | 11.2 |
| 16 | 21.272 | 6.8 |
| 17 | 24.437 | 6.7 |
| 18 | 25.257 | 5.9 |
| 19 | 26.229 | 4.4 |
| 20 | 27.870 | 3.7 |
| 21 | 28.631 | 1.9 |
| 22 | 29.126 | 5.2 |
| 23 | 29.943 | 1.5 |

Figure 5:
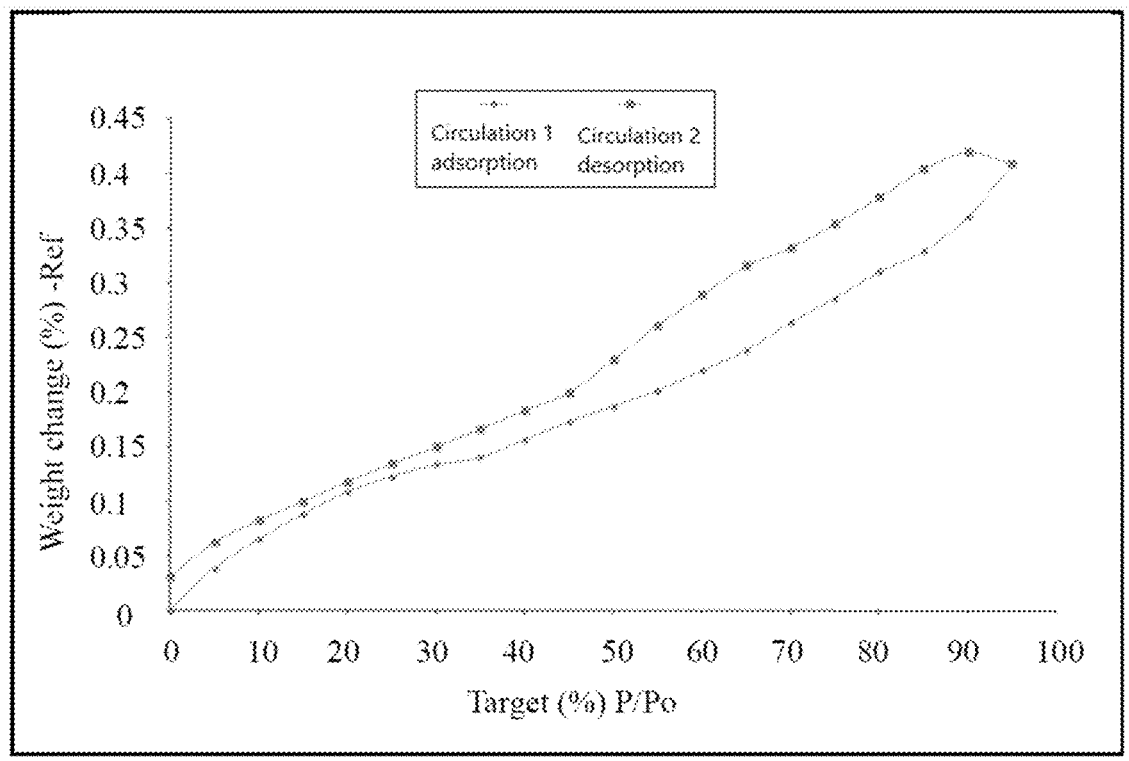
FIG. 5 is the DVS pattern of the crystal form A of the compound as shown in formula I.

Embodiment 8: Dynamic Vapor Sorption (DVS) Analysis of the Crystal Form A (as Shown in FIG. 5)

An appropriate amount of the crystal form A sample of the compound as shown in formula I was weighed and dried at 25° C. and 0% RH for 60 min. The hygroscopic characteristics of the sample were tested when the humidity changed from 0% RH to 95% RH, and the dehumidifying characteristics of the sample were tested when the humidity changed from 95% RH to 0% RH. The humidity change in each step size was 5% RH, the equilibrium standard was that the weight change rate within 10 min was less than 0.01%/min, and the longest equilibrium time was 2 hours. The DVS results showed that the crystal form A had a hygroscopic weight gain of 0.310% at 25° C. and 80% RH humidity, and had a hygroscopic weight gain of 0.409% at 95% RH humidity, indicating that the sample was slightly hygroscopic.

Figure 6:
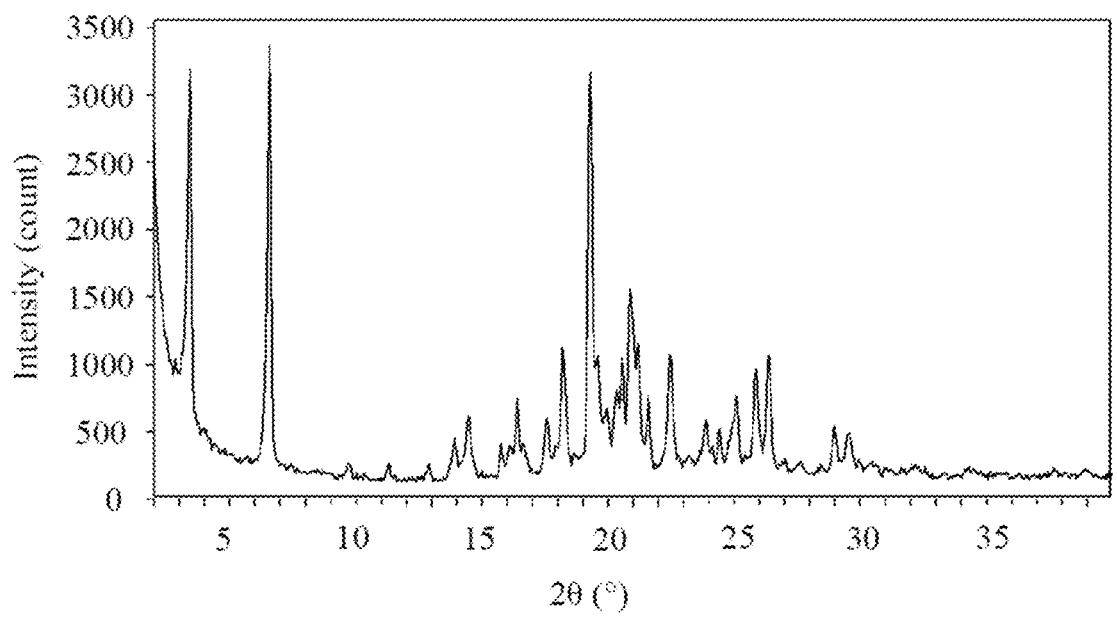
FIG. 6 is the XRPD pattern of the crystal form B of the compound as shown in formula I.

Embodiment 9: X-Ray Powder Diffraction (XRPD) Analysis of the Crystal Form B (as Shown in FIG. 6)

The light source was CuK, the X-ray intensity was 40 KV/40 mA, the scanning mode was Theta-Theta, the scanning angle range was 4° to 40°, the step size was 0.05°, and the scanning speed was 0.5 second/step, and the results are detailed in table 8.

TABLE 8

| Number | 2θ (2θ ± 0.2°) | Relative intensity (%) |
|---|---|---|
| 1 | 3.424 | 89.1 |
| 2 | 6.576 | 100.0 |
| 3 | 9.732 | 3.4 |
| 4 | 11.304 | 3.7 |
| 5 | 12.905 | 3.2 |
| 6 | 13.918 | 8.7 |
| 7 | 14.467 | 13.9 |
| 8 | 16.406 | 17.6 |
| 9 | 17.567 | 11.6 |
| 10 | 18.217 | 26.6 |
| 11 | 19.297 | 87.8 |
| 12 | 20.557 | 16.2 |
| 13 | 20.901 | 35.7 |
| 14 | 22.460 | 24.7 |
| 15 | 23.872 | 8.3 |
| 16 | 25.084 | 12.1 |
| 17 | 25.878 | 20.0 |
| 18 | 26.379 | 25.5 |
| 19 | 28.983 | 10.2 |
| 20 | 29.531 | 8.0 |
| 21 | 30.459 | 1.6 |
| 22 | 32.171 | 2.3 |
| 23 | 34.297 | 2.0 |
| 24 | 37.676 | 1.9 |
| 25 | 38.902 | 1.6 |

Figure 7:
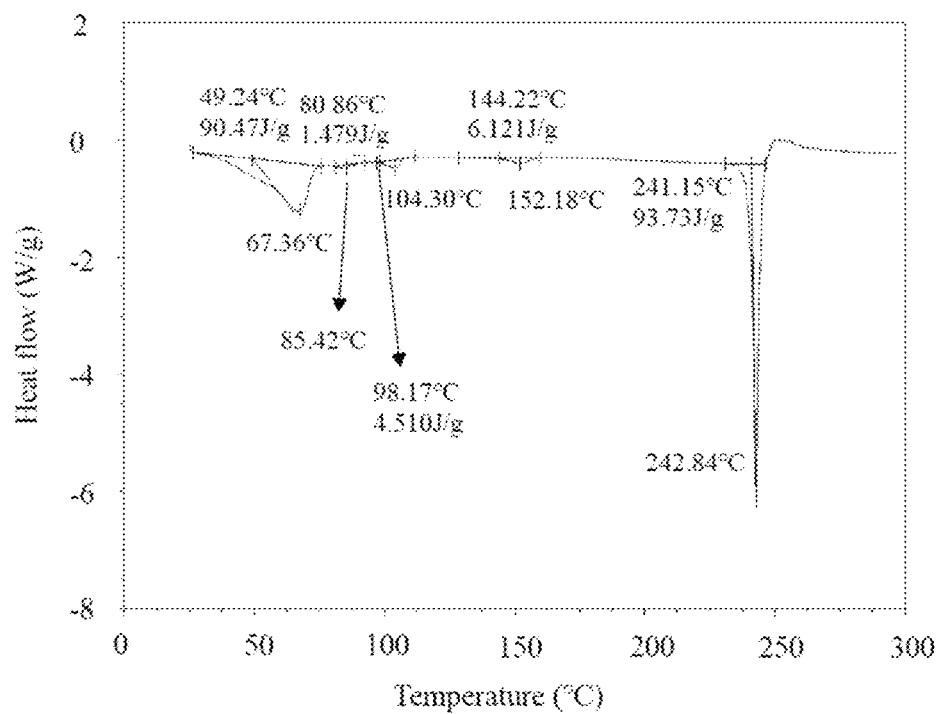
FIG. 7 is the DSC pattern of the crystal form B of the compound as shown in formula I.

Embodiment 10: Differential Scanning Calorimetry (DSC) Analysis of the Crystal Form B (as Shown in FIG. 7)

1.5330 mg of the crystal form B sample of the compound as shown in formula I was weighed, and placed in an unsealed aluminum tray; the sample was equilibrated at 25° C. in a nitrogen flow (50 mL/min), and then heated from 25° C. to 300° C. at a heating rate of 10° C./min, and the results are detailed in table 9.

TABLE 9

| Sample | Initial temperature (° C.) | Maximum temperature (° C.) | Peak area (J/g) |
|---|---|---|---|
| Crystal form B | 49.24 | 67.36 | 90.47 |
|  | 80.86 | 85.42 | 1.479 |
|  | 98.17 | 104.30 | 4.510 |
|  | 241.15 | 242.84 | 93.73 |

Figure 8:
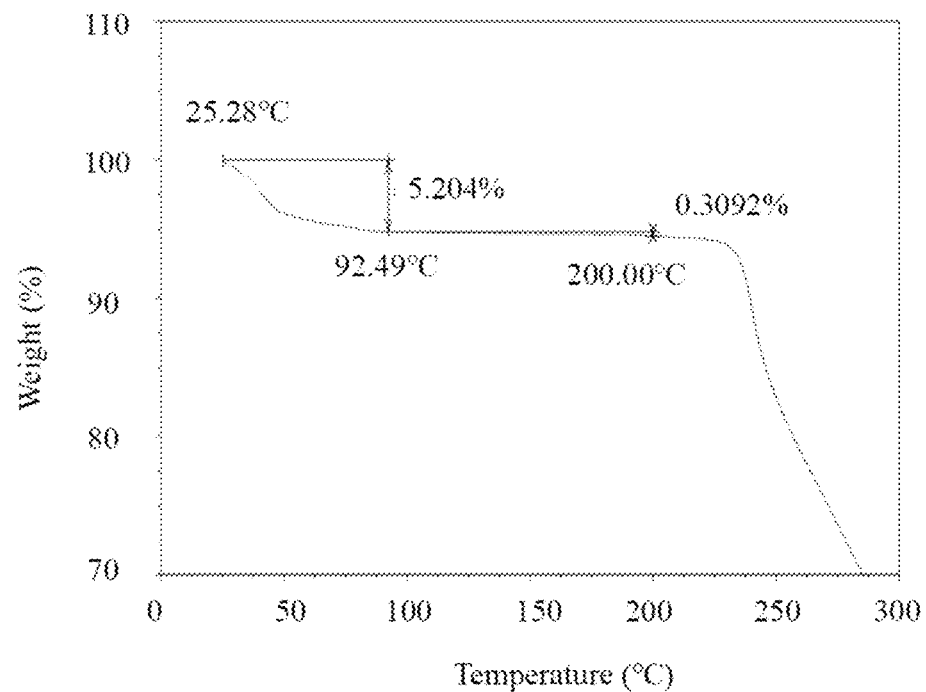
FIG. 8 is the TGA pattern of the crystal form B of the compound as shown in formula I.

Embodiment 11: Thermogravimetric Analysis (TGA) of the Crystal Form B (as Shown in FIG. 8)

1.7310 mg of the crystal form B sample of the compound as shown in formula I was weighed, and placed in a platinum sample tray; in a nitrogen flow (60 mL/min), the sample was heated from 25° C. to 300° C. at a heating rate of 10° C./min, and the initial sample was heated from 25.3° C. to 92.5° C., and the weight loss was 5.2%.

Figure 9:
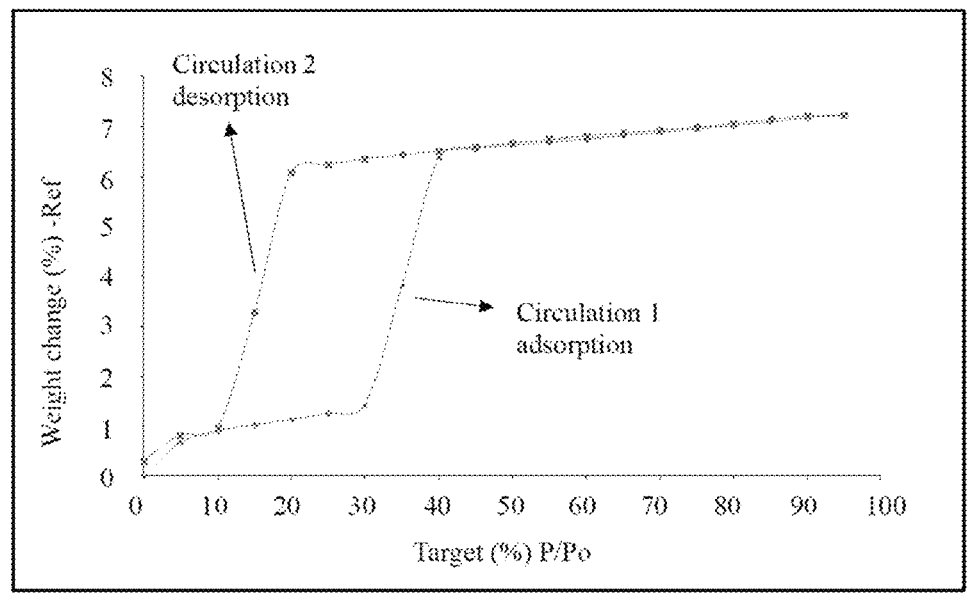
FIG. 9 is the DVS pattern of the crystal form B of the compound as shown in formula I.

Embodiment 12: Dynamic Vapor Sorption (DVS) Analysis of the Crystal Form B (as Shown in FIG. 9)

An appropriate amount of the crystal form B sample of the compound as shown in formula I was weighed and dried at 25° C. and 0% RH for 60 min. The hygroscopic characteristics of the sample were tested when the humidity changed from 0% RH to 95% RH, and the dehumidifying characteristics of the sample were tested when the humidity changed from 95% RH to 0% RH. The humidity change in each step size was 5% RH, the equilibrium standard was that the weight change rate within 5 min was less than 0.01%/min, and the longest equilibrium time was 2 hours. The results showed that the sample had a weight gain of 7.235% from 0% RH to 95% RH, indicating that the sample was hygroscopic.

Figure 10:
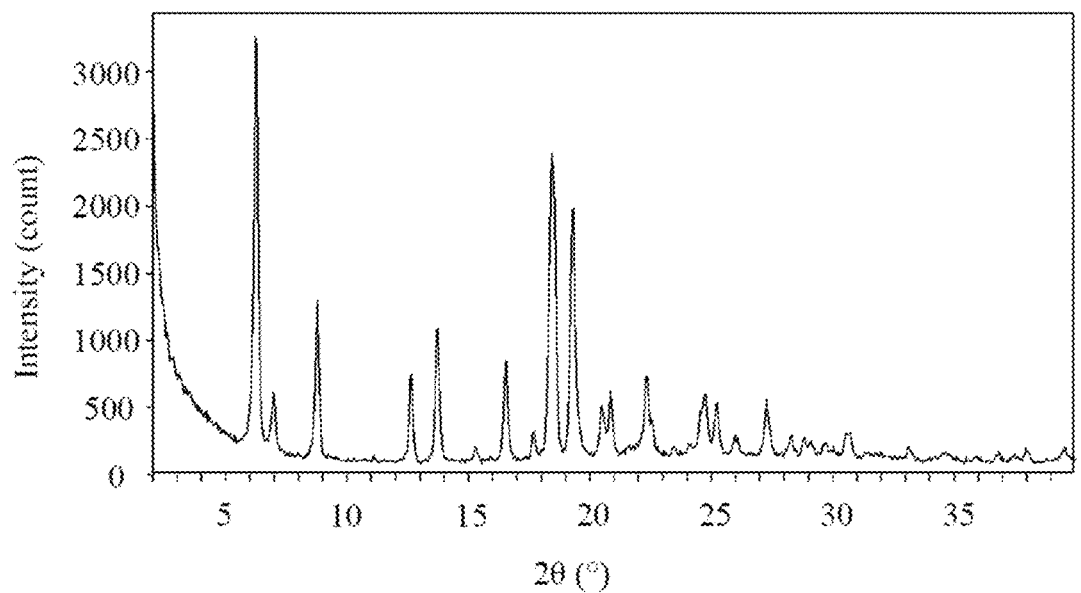
FIG. 10 is the XRPD pattern of the crystal form C of the compound as shown in formula I.

Embodiment 13: X-Ray Powder Diffraction (XRPD) Analysis of the Crystal Form C (as Shown in FIG. 10)

The light source was CuK, the X-ray intensity was 40 KV/40 mA, the scanning mode was Theta-Theta, the scanning angle range was 4° to 40°, the step size was 0.05°, and the scanning speed was 0.5 second/step, and the results are detailed in table 10.

TABLE 10

| Number | 2θ (2θ ± 0.2°) | Relative intensity (%) |
|---|---|---|
| 1 | 6.250 | 100 |
| 2 | 6.979 | 15.3 |
| 3 | 8.779 | 38.6 |
| 4 | 12.635 | 21.3 |
| 5 | 13.720 | 32.6 |
| 6 | 15.285 | 3.1 |
| 7 | 16.525 | 24.1 |
| 8 | 17.696 | 5.5 |
| 9 | 18.458 | 73.0 |
| 10 | 19.302 | 59.0 |
| 11 | 20.852 | 15.4 |
| 12 | 22.345 | 19.1 |
| 13 | 24.772 | 14.3 |
| 14 | 25.230 | 11.5 |
| 15 | 25.996 | 4.1 |
| 16 | 27.285 | 13.2 |

TABLE 10-continued

| Number | 2θ (2θ ± 0.2°) | Relative intensity (%) |
|---|---|---|
| 17 | 28.303 | 4.1 |
| 18 | 28.829 | 3.7 |
| 19 | 29.699 | 2.3 |
| 20 | 30.703 | 5.6 |
| 21 | 33.133 | 3.1 |
| 22 | 34.655 | 1.9 |
| 23 | 36.829 | 2.4 |
| 24 | 37.967 | 3.1 |

Figure 11:
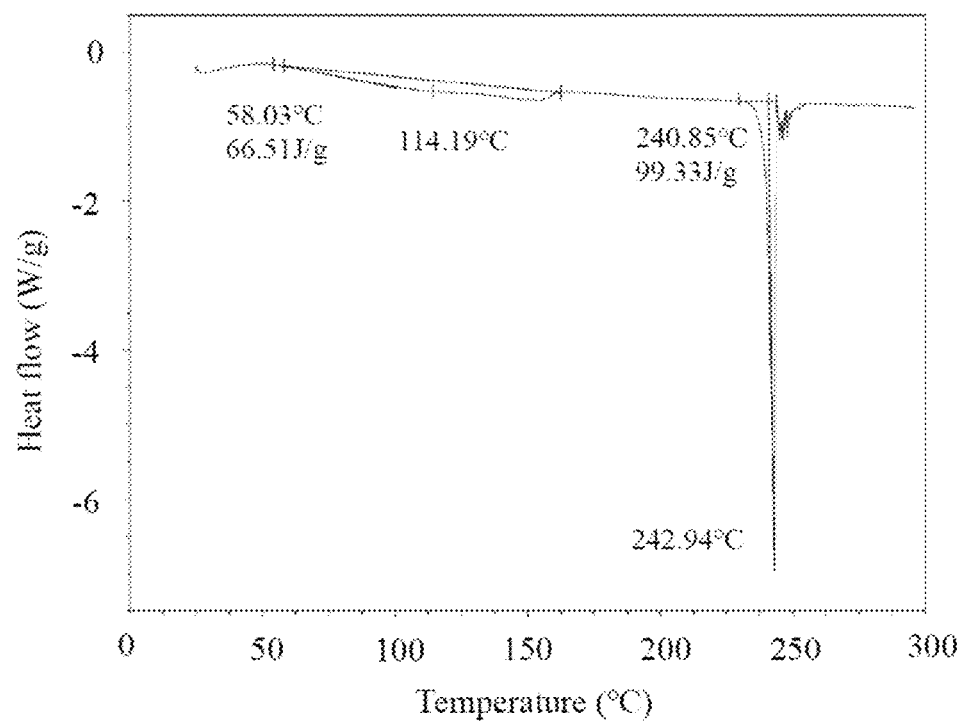
FIG. 11 is the DSC pattern of the crystal form C of the compound as shown in formula I.

Embodiment 14: Differential Scanning Calorimetry (DSC) Analysis of the Crystal Form C (as Shown in FIG. 11)

1.550 mg of the crystal form C sample of the compound as shown in formula I was weighed, and placed in an unsealed aluminum tray; the sample was equilibrated at 25° C. in a nitrogen flow (50 mL/min), and then heated from 25° C. to 300° C. at a heating rate of 10° C./min, and the results are detailed in table 11.

TABLE 11

| Sample | Initial temperature (° C.) | Maximum temperature (° C.) | Peak area (J/g) |
|---|---|---|---|
| Crystal form C | 58.03 | 114.19 | 66.51 |
|  | 240.85 | 242.94 | 99.33 |

Figure 12:
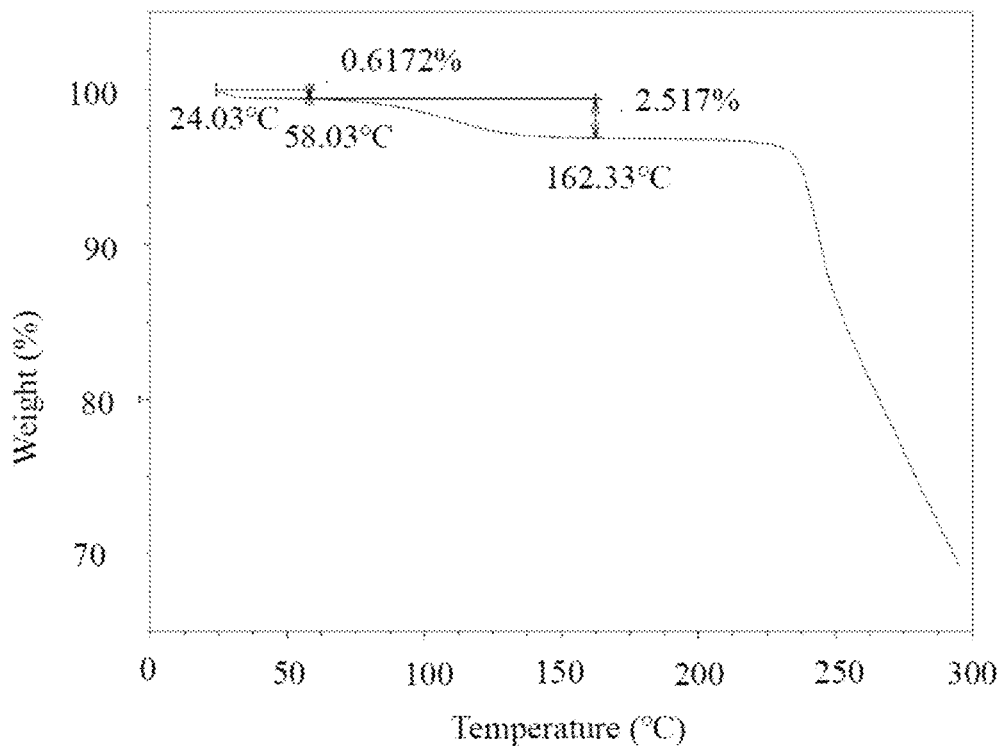
FIG. 12 is the TGA pattern of the crystal form C of the compound as shown in formula I.

Embodiment 15: Thermogravimetric Analysis (TGA) of the Crystal Form C (as Shown in FIG. 12)

5.3570 mg of the crystal form C sample of the compound as shown in formula I was weighed, and placed in a platinum sample tray; in a nitrogen flow (60 mL/min), the sample was heated from 25° C. to 300° C. at a heating rate of 10° C./min; the sample was heated from 24.0° C. to 58.0° C., and the weight loss was 0.62%; the sample was heated from 58.0° C. to 162.3° C., and the weight loss was 2.5%. The sample was heated to 200° C., and the crystal form C was converted into the crystal form A, and the results are detailed in table 12.

TABLE 12

| Sample | Initial temperature (° C.) | End temperature (° C.) | Weight loss (%) |
|---|---|---|---|
| Crystal form C | 24.03 | 58.03 | 0.6172 |
|  | 58.03 | 162.33 | 2.517 |

Figure 13:
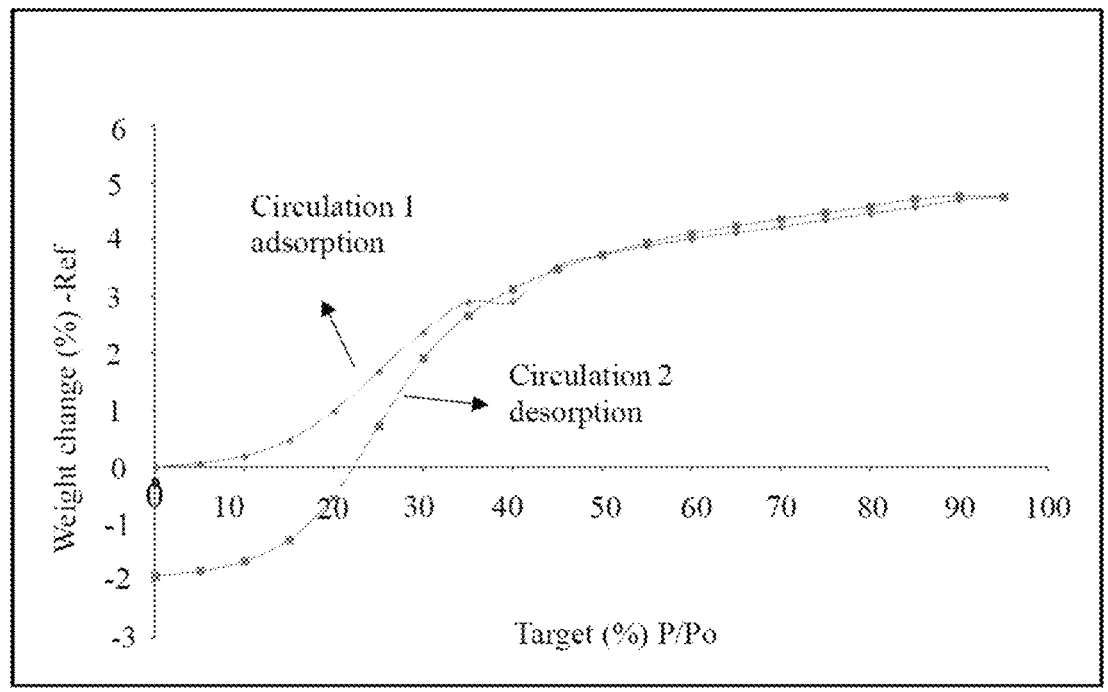
FIG. 13 is the DVS pattern of the crystal form C of the compound as shown in formula I.

Embodiment 16: Dynamic Vapor Sorption (DVS) Analysis of the Crystal Form C (as Shown in FIG. 13)

An appropriate amount of the crystal form C sample of the compound as shown in formula I was weighed and dried at 25° C. and 0% RH for 60 min. The hygroscopic characteristics of the sample were tested when the humidity changed from 0% RH to 95% RH, and the dehumidifying characteristics of the sample were tested when the humidity changed from 95% RH to 0% RH. The humidity change in each step size was 5% RH, the equilibrium standard was that the weight change rate within 5 min was less than 0.01%/min, and the longest equilibrium time was 2 hours. The results showed that the sample had a weight gain of 4.767% from 0% RH to 95% RH, indicating that the sample was hygroscopic.

Embodiment 17: Comparison of Equilibrium Solubility and Dissolution Rate of Crystal Forms A, B and C To further study whether the equilibrium solubility and dissolution rate of crystal forms A, B and C are different in pure water and physiological related media in vivo, the equilibrium solubility and dissolution rate of four crystal forms in water, simulated gastric fluid (SGF), fasted-state simulated intestinal fluid (FaSSIF) and fed state simulated intestinal fluid (FeSSIF) were tested respectively. About 20 mg of samples A, B, and C were weighed and added to a 4 mL glass bottle, respectively, and 3 mL of medium was added in turn, respectively; the mixture was sonicated for 15 seconds, put in a shaker at 37° C. with a rotation speed of 200 rpm, and about 1 mL of the suspension was taken at 0.5 hours, 2 hours and 24 hours, respectively, centrifuged with a rotation speed of 12000 rpm for 5 min; if necessary, the supernatant was diluted (diluent: methanol/water=9/1) to a suitable multiple, or directly measured the concentration by HPLC, and the solubility value of each sample was calculated. The solubility test results at each time point are shown in table 13:

TABLE 13

| Time Crystal form-medium | 0.5 hours Solubility (μg/mL) | 2 hours Solubility (μg/mL) | 24 hours Solubility (μg/mL) |
|---|---|---|---|
| A-Water | 1.5 | 6.0 | 6.1 |
| B-Water | 2.5 | 7.5 | 1.2 |
| C-Water | 1.7 | 6.5 | 1.8 |
| A-SGF | 0.4 | 0.3 | 0.1 |
| B-SGF | 0.5 | 0.1 | 0.2 |
| C-SGF | 0.3 | 0.2 | 0.5 |
| A-FaSSIF | 8.7 | 2.0 | 4.3 |
| B-FaSSIF | 13.3 | 8.8 | 8.6 |
| C-FaSSIF | 9.1 | 2.2 | 4.5 |
| A-FaSSIF | 182.8 | 176.6 | 170.4 |
| B-FaSSIF | 176.4 | 175.9 | 179.7 |
| C-FaSSIF | 181.7 | 174.3 | 166.6 |

Remarks: SGF: simulated gastric fluid; FaSSIF: fasted-state simulated intestinal fluid; FeSSIF: fed state simulated intestinal fluid The solubility test results showed that there was no significant difference in the dissolution rate and solubility of the three crystal forms in water, SGF, FaSSIF and FeSSIF.

Embodiment 18: Solid-State Stability Experiment of Crystal Forms a, B and C

The samples of crystal forms A, B, and C were weighed and added to a 20 mL colorless transparent glass bottle, respectively, and the sample bottles were respectively placed under the corresponding influencing factors and acceleration conditions (the sample bottles under humidity conditions were sealed with tin foil and placed with holes, and the other samples were covered tightly and placed), taken out after being placed for 1 week and 2 weeks respectively, and the sample content and related substances under various conditions were detected by HPLC; according to the same method as above, samples were respectively weighed and placed under a corresponding influencing factor and accelerated condition, and were taken out after being placed for 2 weeks for observing the appearance and XRPD characterization of each sample, and the physical stability of each crystal form was examined, and the test methods are detailed in table 14 and table 15; at the same time, 2 samples of the crystal forms A, B, and C of the compound as shown in formula I were respectively weighed accurately into 20 mL colorless transparent glass bottles and covered tightly, placed in a −20° C. refrigerator, and taken out as a standard for HPLC analysis at 2 weeks, and the test results are detailed in table 16 and table 17.

TABLE 14

Content liquid chromatography method for solid stability investigation

| Chromatographic column | Waters Xbridge C18 | | |
|---|---|---|---|
| Mobile phase | A: 100 % pure water; B: 100 % methanol | | |
| Gradient elution | Time (minutes) | Percentage of phase A | Percentage of phase B |
| program | 0 | 30 | 70 |
| | 13 | 10 | 90 |
| | 18 | 10 | 90 |
| | 18.1 | 30 | 70 |
| | 25 | 30 | 70 |
| Flow rate | 1.0 mL/min | | |
| Column temperature | 40° C. | | |
| Detection wavelength | 220 nm | | |
| Running time | 25 min | | |
| Injection volume | 10 μL | | |
| Diluent | Methanol: acetonitrile = 50:50 | | |
| Sample concentration | 0.3 mg/mL | | |

TABLE 15

Related substances liquid chromatography method for solid stability investigation

| Chromatographic column | Waters Xbridge ™ C18 (4.6 × 150 mm, 3.5 μm) | | |
|---|---|---|---|
| Mobile phase | A: 100 % pure water; B: 100 % methanol | | |
| Gradient elution program | Time (minutes) | | |
| | 0 | 40 | 60 |
| | 5 | 40 | 60 |
| | 30 | 20 | 80 |
| | 60 | 20 | 80 |
| Flow rate | 1.0 mL/min | | |
| Column temperature | 40° C. | | |
| Detection wavelength | 220 nm | | |
| Running time | 60 min | | |
| Injection volume | 5 μL | | |
| Diluent | Methanol: acetonitrile = 50:50 | | |
| Sample concentration | 1.5 mg/mL | | |

Embodiment 16: Solid-State Stability Results of Crystal Forms a, B and C-Content and Related Substances

| Sample name | Condition | Time | Content (%) | Total related substances (%) |
|---|---|---|---|---|
| Crystal form A-Control | −20° C. | 2 weeks | / | 0.00 |
| Crystal form A | High temperature (60° C.) | 1 week | 100.69 | 0.02 |
| | | 2 weeks | 104.03 | 0.03 |
| | High humidity (92.5% RH) | 1 week | 104.75 | 0.10 |
| | | 2 weeks | 104.25 | 0.12 |
| | illumination (4500 LuX) | 1 week | 96.10 | 3.94 |
| | | 2 weeks | 88.50 | 11.18 |
| | Acceleration (40° C./75% RH) | 1 week | 104.34 | 0.04 |
| | | 2 weeks | 104.13 | 0.03 |
| Crystal form B-Control | −20° C. | 2 weeks | / | 0.00 |
| Crystal form B | High temperature (60° C.) | 1 week | 100.70 | 0.00 |
| | | 2 weeks | 100.15 | 0.00 |
| | High humidity (92.5% RH) | 1 week | 100.09 | 0.00 |
| | | 2 weeks | 100.83 | 0.00 |
| | illumination (4500 LuX) | 1 week | 100.02 | 0.39 |
| | | 2 weeks | 99.69 | 1.28 |
| | Acceleration (40° C./75% RH) | 1 week | 103.22 | 0.00 |
| | | 2 weeks | 101.60 | 0.00 |
| Crystal form C-Control | −20° C. | 2 weeks | 100.00 | 0.00 |
| Crystal form C | High temperature (60° C.) | 1 week | 98.41 | 0.00 |
| | | 2 weeks | 100.18 | 0.00 |
| | High humidity (92.5% RH) | 1 week | 101.55 | 0.00 |
| | | 2 weeks | 100.59 | 0.00 |
| | illumination (4500 LuX) | 1 week | 102.18 | 0.52 |
| | | 2 weeks | 98.64 | 1.56 |
| | Acceleration (40° C./75% RH) | 1 week | 100.06 | 0.00 |
| | | 2 weeks | 99.89 | 0.00 |

Embodiment 17: Solid-State Stability Results of Crystal Forms a, B and C-Appearance and Crystal Forms

| | Stability investigation | Characterization results | |
|---|---|---|---|
| Sample name | condition | Appearance | Crystal form |
| Crystal form A-Control | −20° C. | Off-white | Crystal form A |
| Crystal form A | High temperature (60° C.) | Off-white | Crystal form A |
| | Illumination (4500 Lux) | Off-white | Crystal form A |
| | High humidity (92.5% RH) | Off-white | Crystal form A |
| | Acceleration (40° C./75% RH) | Off-white | Crystal form A |

| Sample name | Stability investigation condition | Characterization results Appearance | Crystal form |
| --- | --- | --- | --- |
| Crystal form B-Control | −20° C. | Off-white | Crystal form B |
| Crystal form B | High temperature (60° C.) | Off-white | Mixed crystal form |
| | Illumination (4500 Lux) | Off-white | Crystal form B |
| | High humidity (92.5% RH) | Off-white | Crystal form B |
| | Acceleration (40° C./75% RH) | Off-white | Crystal form B |
| Crystal form C-Control | −20° C. | Off-white | Crystal form C |
| Crystal form C | High temperature (60° C.) | Off-white | Crystal form C |
| | Illumination (4500 Lux) | Off-white | Crystal form C |
| | High humidity (92.5% RH) | Off-white | Crystal form C |
| | Acceleration (40° C./75% RH) | Off-white | Crystal form C |

CONCLUSION

The samples of crystal forms A, B and C placed under four conditions of high temperature, high humidity, illumination and acceleration for 2 weeks had the same appearance as the initial samples, and they were all off-white; there was no significant difference between the crystal form A and C and the initial sample, and the physical stability was good, while the crystal form B was converted into other crystal form at a high temperature (60° C.) and the physical stability was poor.

Crystal forms A, B and C were significantly affected by illumination, and the total related substances increased by 11.18%, 1.28% and 1.56% respectively at 2 weeks, indicating that illumination has a significant effect on crystal forms A, B and C, and the crystal forms A, B and C are necessary to protect from light.

Comparative Embodiment 1: Preparation of Crystal Form V (Suspension Equilibrium Method)

Figure 14:
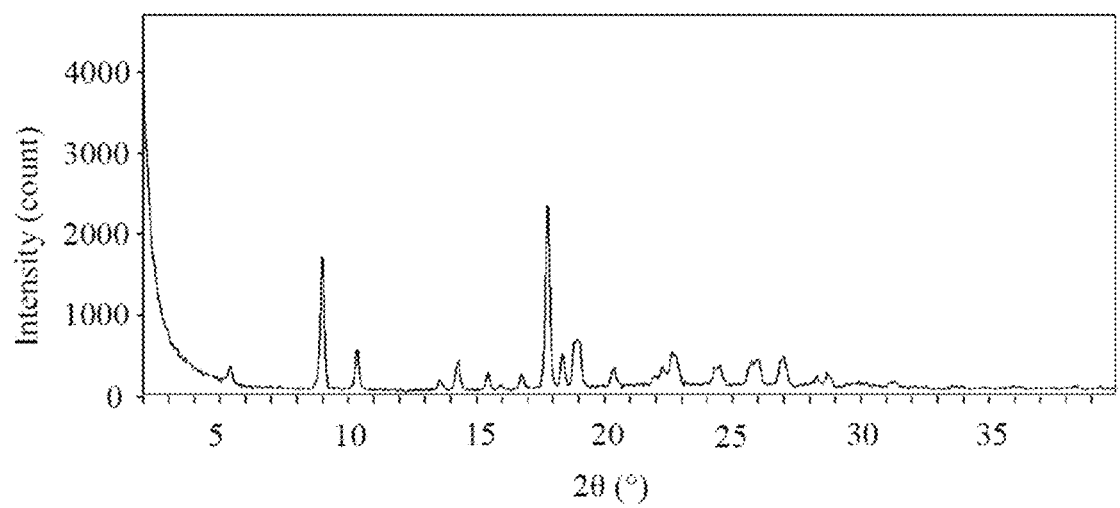
FIG. 14 is the XRPD pattern of the crystal form V of the compound as shown in formula I.
Figure 15:
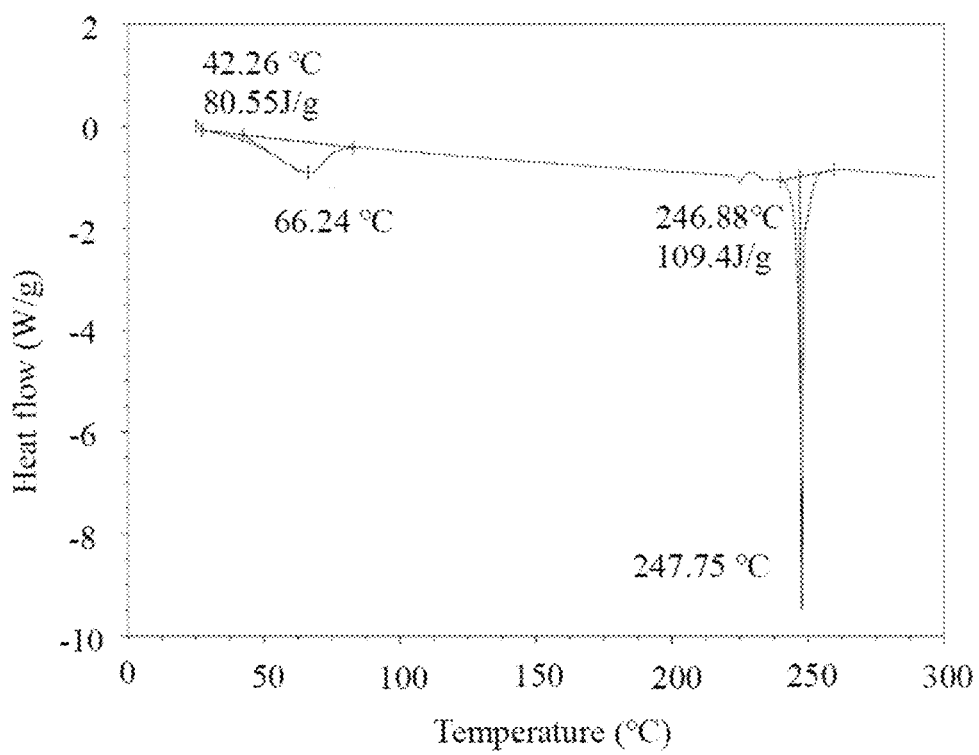
FIG. 15 is the DSC pattern of the crystal form V of the compound as shown in formula I.

100 mg of the compound as shown in formula I sample was weighed and added to a bottle, then 20 times the volume of methanol was added to the bottle, and the mixture was magnetic stirred and slurried for 14 days at room temperature. The solution was centrifuged, and the solid was collected, and dried at 40° C. for 4 hours, and the solid after drying was characterized, and the crystal form was defined as a crystal form V; the XRPD pattern of the crystal form V is as shown in FIG. 14, and the DSC pattern of the crystal form V is as shown in FIG. 15; the crystal form V was heated to 85° C., and the crystal form V was converted into the crystal form A.

Figure 16:
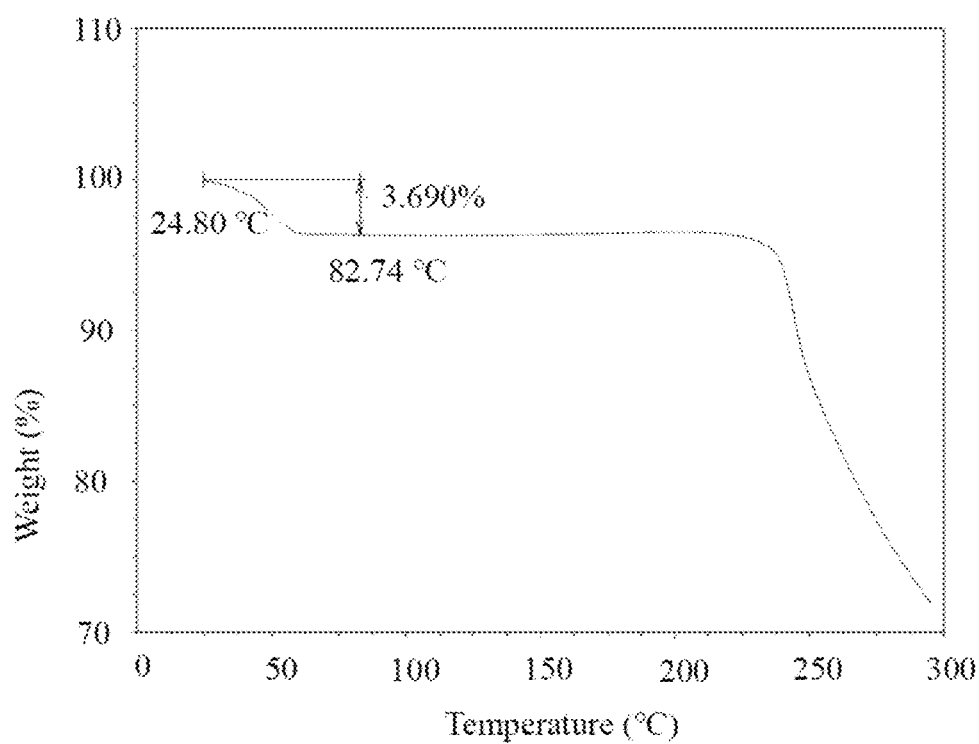
FIG. 16 is the TGA pattern of the crystal form V of the compound as shown in formula I.

FIG. 16 is the TGA pattern of the crystal form V (as shown in FIG. 16, the sample has a weight loss of 3.690% when heated from 24.8° C. to 82.7° C.).

Comparative Embodiment 2: Preparation of Crystal Form VII (Solution Heating-Slow Cooling Method)

Figure 17:
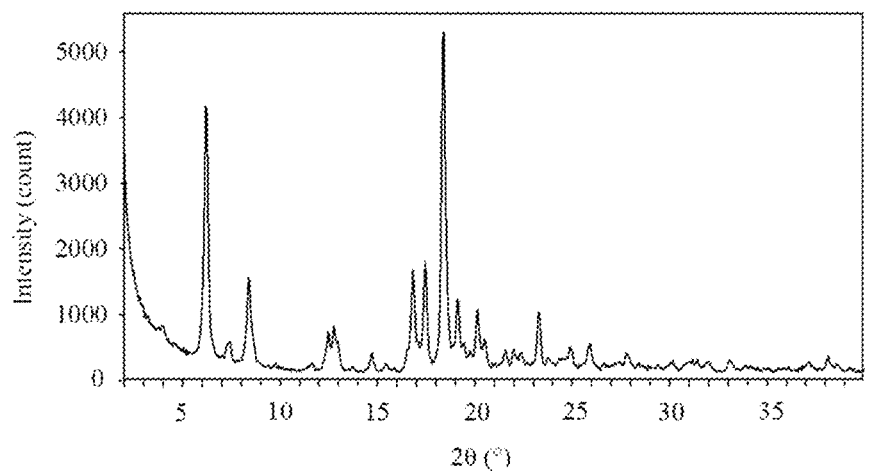
FIG. 17 is the XRPD pattern of the crystal form VII of the compound as shown in formula I.

100 mg of the compound as shown in formula I sample was weighed and added to a glass bottle, and 100 times the volume of ethyl acetate (EA) and 20 times the volume of methanol (MeOH) were added to the bottle, and the sample was placed on a magnetic heating stirrer. The mixture was magnetic stirred to fully dissolve at a water bath of 50° C., filtered and the filtrate was slowly cooled to room temperature at a rate of 6° C./h, overnight, filtered under reduced pressure, and the solid was dried at 70° C. for 4 hours. The solid after drying was characterized, and the crystal form was defined as a crystal form VII; the XRPD pattern of the crystal form VII is as shown in FIG. 17, the sample was heated to 200° C. and cooled to room temperature to characterize XRPD, and the result showed that the crystal form VII was converted into the crystal form A.

Figure 18:
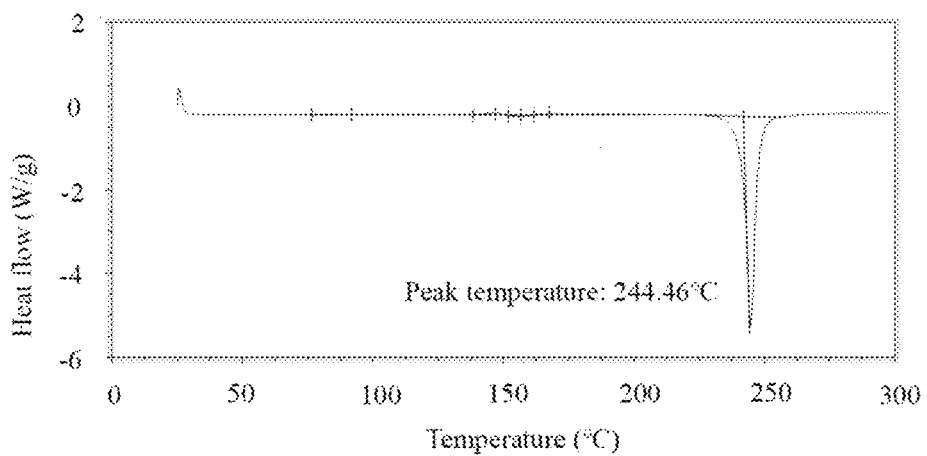
FIG. 18 is the DSC pattern of the crystal form VII of the compound as shown in formula I.

FIG. 18 is the DSC pattern of the crystal form VII (as shown in FIG. 18, the DSC heat flow curve shows that the initial melting point is 241.9° C., and there are several endothermic and exothermic peaks before 200° C.).

Figure 19:
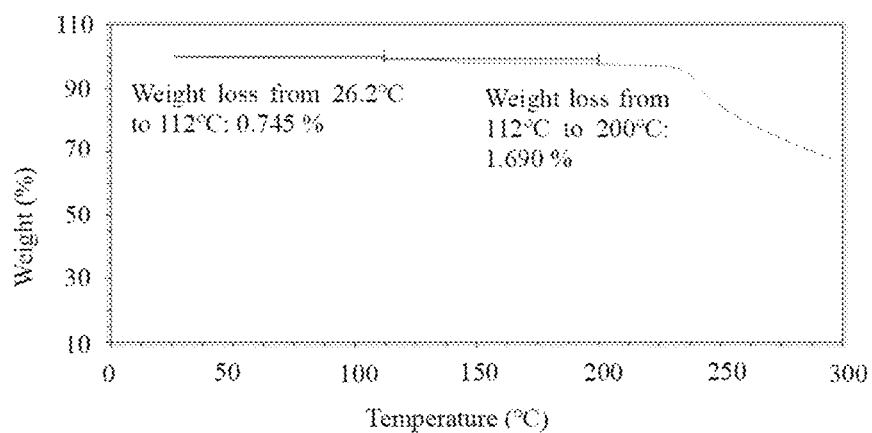
FIG. 19 is the TGA pattern of the crystal form VII of the compound as shown in formula I.

FIG. 19 is the TGA pattern of the crystal form VII (as shown in FIG. 19, the sample has a weight loss of 0.75% when heated from 26.2° C. to 112° C. and a weight loss of 1.69% when heated from 112° C. to 200° C.).

Comparative Embodiment 3: Preparation of Crystal Form VIII (Suspension Equilibrium Method)

Figure 20:
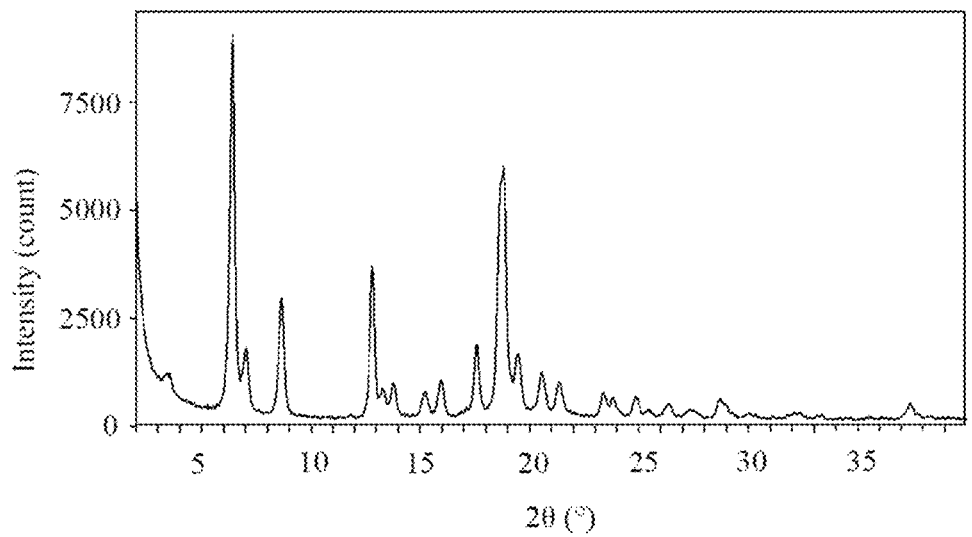
FIG. 20 is the XRPD pattern of the crystal form VIII of the compound as shown in formula I.

100 mg of the compound as shown in formula I sample was weighed and added to a bottle, then 30 times the volume of acetonitrile (ACN) (sample mass (g)×volume multiples) was added to the bottle, and the mixture was magnetic stirred and slurried for 2 days at room temperature, filtered under reduced pressure, and the solid was collected, and dried at 40° C. for 4 hours. The solid after drying was characterized, and the crystal form was defined as a crystal form VIII, and the XRPD pattern of the crystal form VIII is as shown in FIG. 20. The sample was heated to 180° C., and the crystal form VIII sample was converted into the crystal form A.

Figure 21:
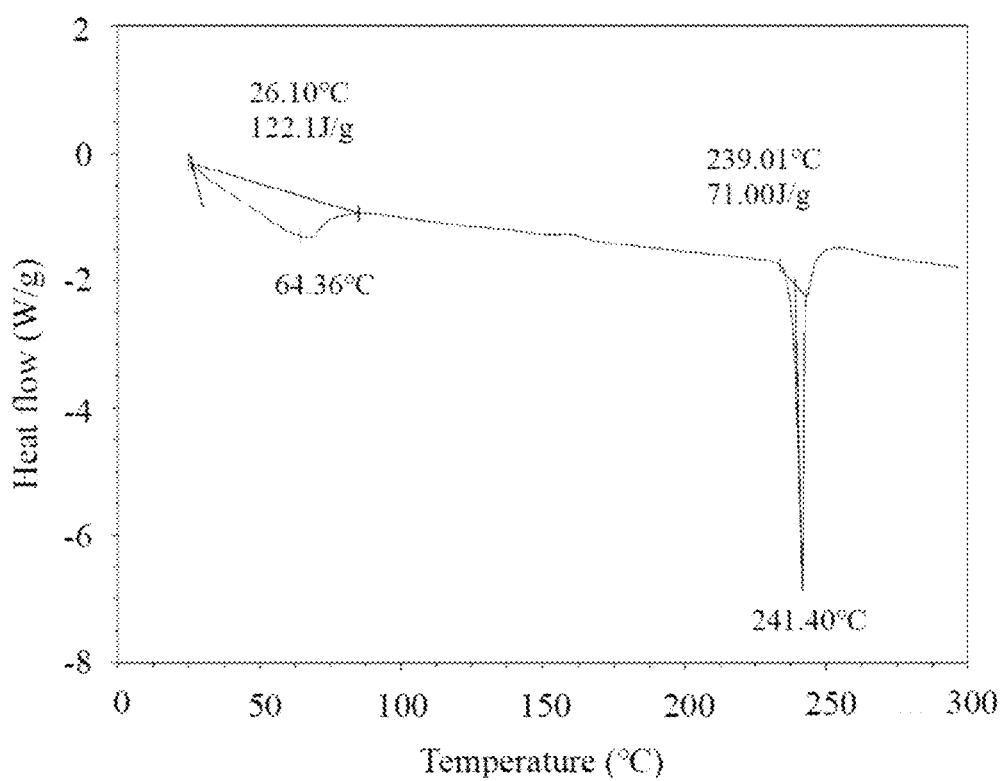
FIG. 21 is the DSC pattern of the crystal form VIII of the compound as shown in formula I.

FIG. 21 is the DSC pattern of the crystal form VIII (as shown in FIG. 21, the DSC heat flow curve shows that the initial melting point is 239.0° C., and there is a broad endothermic peak before 100° C.).

Figure 22:
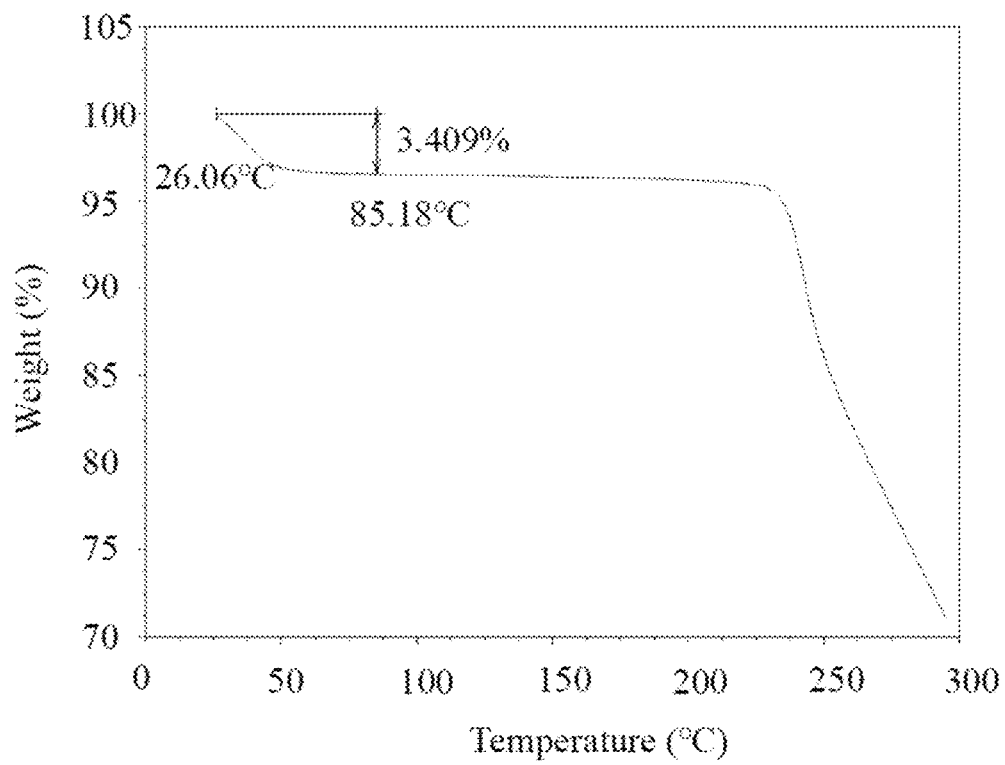
FIG. 22 is the TGA pattern of the crystal form VIII of the compound as shown in formula I.

FIG. 22 is the TGA pattern of the crystal form VIII (as shown in FIG. 22, the sample has a weight loss of 3.409% when heated from 26.1° C. to 85.2° C.).

Comparative Embodiment 4: Preparation of Crystal Form IX (Solution Heating-Slow Cooling Method)

Figure 23:
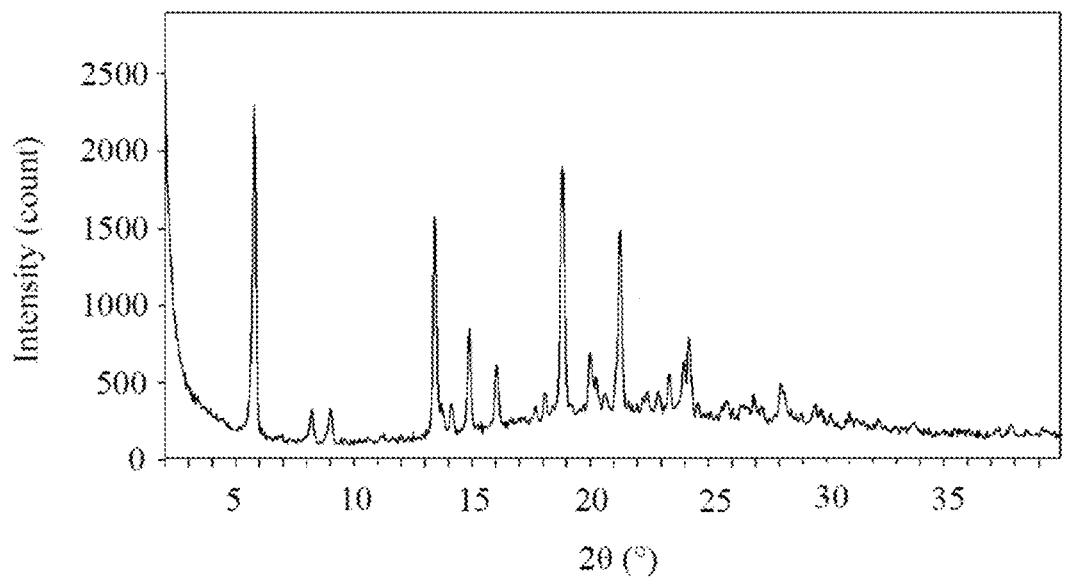
FIG. 23 is the XRPD pattern of the crystal form IX of the compound as shown in formula I.

100 mg of the compound as shown in formula I sample was weighed and added to a glass bottle, and 30 times the volume of N,N-dimethylacetamide (DMA) was added to the bottle, and the sample was placed on a magnetic heating stirrer. The mixture was magnetic stirred to fully dissolve at a water bath of 50° C., filtered, and the filtrate was slowly cooled to room temperature at a rate of 6° C./h, filtered under reduced pressure, and the solid was dried at 70° C. for 4 hours. The solid after drying was characterized, and the crystal form was defined as a crystal form IX, and the XRPD pattern of the crystal form IX is as shown in FIG. 23. The sample was heated to 180° C., and the crystal form IX sample was converted into the crystal form A.

Figure 24:
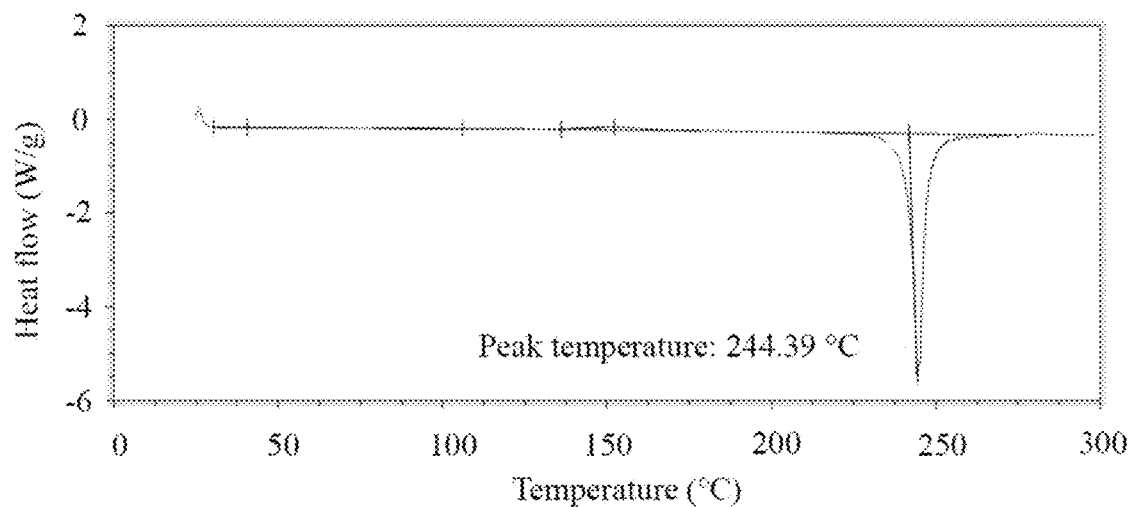
FIG. 24 is the DSC pattern of the crystal form IX of the compound as shown in formula I.

FIG. 24 is the DSC pattern of the crystal form IX (as shown in FIG. 24, the DSC heat flow curve shows that the initial melting point is 241.8° C., and there are several endothermic and exothermic peaks before 200° C.).

Figure 25:
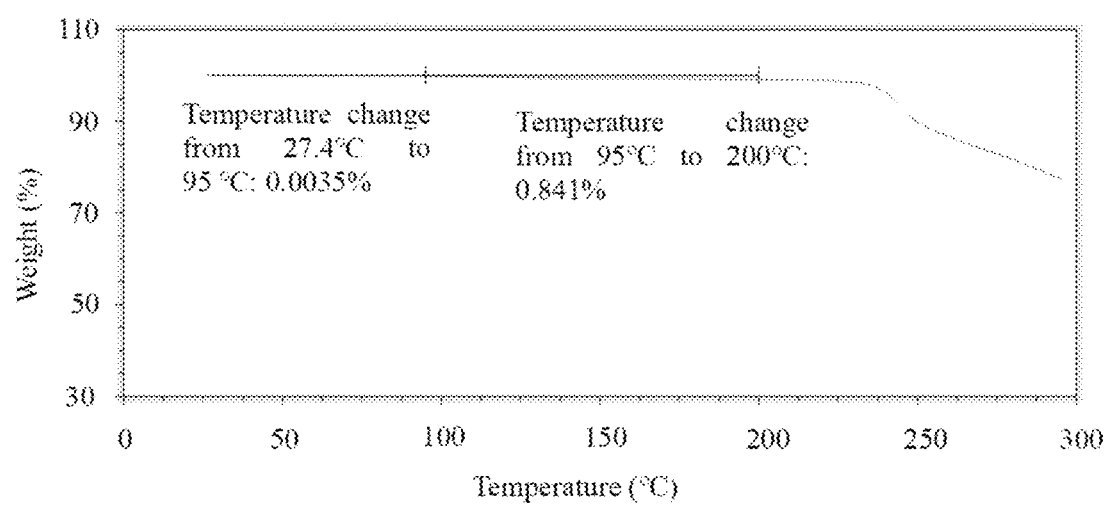
FIG. 25 is the TGA pattern of the crystal form IX of the compound as shown in formula I.

FIG. 25 is the TGA pattern of the crystal form IX (as shown in FIG. 25, the sample has a weight loss of 0.035% when heated from 27.4° C. to 95° C. and a weight loss of 0.841% when heated from 95° C. to 200° C.).

What is claimed is:

1. A crystal form A of a compound as shown in formula I, the X-ray powder diffraction pattern of the crystal form A represented by 2θ angles has characteristic peaks at: 9.923±0.2°, 10.883±0.2° and 17.357±0.2°;

or, has characteristic peaks at 3.979±0.2°, 9.923±0.2°, 10.883±0.2°, 17.357±0.2°, 18.607±0.2° and 19.294±0.2°;

or, has characteristic peaks at 3.979±0.2°, 4.991±0.2°, 9.923±0.2°, 10.883±0.2°, 14.251±0.2°, 16.210±0.2°, 17.357±0.2°, 18.607±0.2°, 19.294±0.2°, 19.594±0.2° and 20.792±0.2°;

or, has characteristic peaks at 3.979±0.2°, 4.991±0.2°, 7.113±0.2°, 8.135±0.2°, 9.923±0.2°, 10.883±0.2°, 11.613±0.2°, 14.251±0.2°, 14.866±0.2°, 16.210±0.2°, 17.357±0.2°, 18.607±0.2°, 19.294±0.2°, 19.594±0.2°, 20.792±0.2°, 21.272±0.2°, 24.437±0.2°, 25.257±0.2°, 26.2295±0.2°, 27.870±0.2°, 28.631±0.2°, 29.126±0.2° and 29.943±0.2°

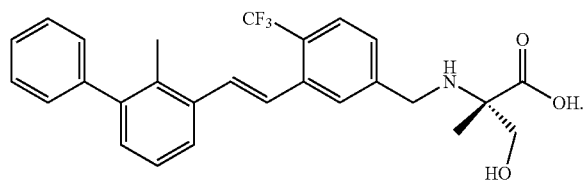

I

2. The crystal form A of the compound as shown in formula I as defined in claim 1, wherein, in the X-ray powder diffraction pattern of the crystal form A represented by 2θ angles, the 2θ values are as shown in the following table,

| 2θ (2θ ± 0.2°) | Relative intensity (%) |
|---|---|
| 3.979 | 25.2 |
| 4.991 | 14.3 |
| 7.113 | 1.5 |
| 8.135 | 1.5 |
| 9.923 | 36.3 |
| 10.883 | 27.0 |
| 11.613 | 6.6 |
| 14.251 | 13.2 |
| 14.866 | 4.4 |
| 16.210 | 18.0 |
| 17.357 | 100.0 |
| 18.607 | 25.0 |
| 19.294 | 26.3 |
| 19.594 | 11.4 |
| 20.792 | 11.2 |
| 21.272 | 6.8 |
| 24.437 | 6.7 |
| 25.257 | 5.9 |
| 26.229 | 4.4 |
| 27.870 | 3.7 |
| 28.631 | 1.9 |
| 29.126 | 5.2 |
| 29.943 | 1.5; | or, in the polarized light microscope analysis of the crystal form A, the shape of the crystal form is granular or rod-shaped; and the particle size of the crystal form A is 10 to 100 μm;

or, in the differential scanning calorimetry analysis of the crystal form A, the differential scanning calorimetry analysis of the crystal form A has a thermal absorption peak at 247° C.; and the melting heat is 118.0 J/g;

or, in the thermogravimetric analysis of the crystal form A, the sample has a weight loss of only 0.1447% from 26.76° C. to 119.97° C., and the "%" is the weight percentage;

or, in the dynamic vapor sorption analysis of the crystal form A, the hygroscopic weight gain is 0.310% at 80% RH and the hygroscopic weight gain is 0.409% at 95% RH.

3. A crystal form B of the compound as shown in formula I, the X-ray powder diffraction pattern of the crystal form B represented by 2θ angles has characteristic peaks at 3.424±0.2°, 6.576±0.2° and 19.297±0.2°;

or, has characteristic peaks at 3.424±0.2°, 6.576±0.2°, 18.217±0.2°, 19.297±0.2°, 20.901±0.2° and 26.379±0.2°;

or, has characteristic peaks at 3.424±0.2°, 6.576±0.2°, 14.467±0.2°, 16.406±0.2°, 17.567±0.2°, 18.217±0.2°, 19.297±0.2°, 20.557±0.2°, 20.901±0.2°, 22.460±0.2°, 25.084±0.2°, 25.878±0.2°, 26.379±0.2° and 28.983±0.2°;

or, has characteristic peaks at 3.424±0.2°, 6.576±0.2°, 9.732±0.2°, 11.304±0.2°, 12.905±0.2°, 13.918±0.2°, 14.467±0.2°, 16.406±0.2°, 17.567±0.2°, 18.217±0.2°, 19.297±0.2°, 20.557±0.2°, 20.901±0.2°, 22.460±0.2°, 23.872±0.2°, 25.084±0.2°, 25.878±0.2°, 26.379±0.2°, 28.983±0.2°, 29.531±0.2°, 30.459±0.2°, 32.171±0.2°, 34.297±0.2°, 37.676±0.2° and 38.902±0.2°,

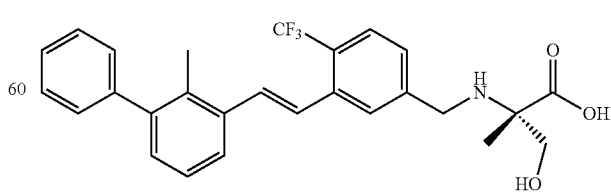

I

4. The crystal form B of the compound as shown in formula I as defined in claim 3, wherein, in the X-ray powder diffraction pattern of the crystal form B represented by 2θ angles, the 2θ values are as shown in the following table,

| 2θ (2θ ± 0.2°) | Relative intensity (%) |
|---|---|
| 3.424 | 89.1 |
| 6.576 | 100.0 |
| 9.732 | 3.4 |
| 11.304 | 3.7 |
| 12.905 | 3.2 |
| 13.918 | 8.7 |
| 14.467 | 13.9 |
| 16.406 | 17.6 |
| 17.567 | 11.6 |
| 18.217 | 26.6 |
| 19.297 | 87.8 |
| 20.557 | 16.2 |
| 20.901 | 35.7 |
| 22.460 | 24.7 |
| 23.872 | 8.3 |
| 25.084 | 12.1 |
| 25.878 | 20.0 |
| 26.379 | 25.5 |
| 28.983 | 10.2 |
| 29.531 | 8.0 |
| 30.459 | 1.6 |
| 32.171 | 2.3 |
| 34.297 | 2.0 |
| 37.676 | 1.9 |
| 38.902 | 1.6; | or, in the differential scanning calorimetry analysis of the crystal form B, the differential scanning calorimetry analysis of the crystal form B has a thermal absorption peak at 243° C.; and the melting heat is 93.73 J/g;

or, in the thermogravimetric analysis of the crystal form B, the sample has a weight loss of 5.2% from 25.3° C. to 92.5° C., and the "%" is the weight percentage;

or, in the dynamic vapor sorption analysis of the crystal form B, the sample has a weight gain of 7.235% from 0% RH to 95% RH.

5. A crystal form C of the compound as shown in formula I, the X-ray powder diffraction pattern of the crystal form C represented by 2θ angles has characteristic peaks at 6.250±0.2°, 18.458±0.2° and 19.302±0.2°;

or, has characteristic peaks at 6.250±0.2°, 8.779±0.2°, 13.720±0.2°, 18.458±0.2° and 19.302±0.2°;

or, has characteristic peaks at 6.250±0.2°, 8.779±0.2°, 12.635±0.2°, 13.720±0.2°, 16.525±0.2°, 18.458±0.2° and 19.302±0.2°;

or, has characteristic peaks at 6.250±0.2°, 6.979±0.2°, 8.779±0.2°, 12.635±0.2°, 13.720±0.2°, 16.525±0.2°, 18.458±0.2°, 19.302±0.2°, 20.852±0.2°, 22.345±0.2°, 24.772±0.2°, 25.230±0.2° and 27.285±0.2°;

or, has characteristic peaks at 6.250±0.2°, 6.979±0.2°, 8.779±0.2°, 12.635±0.2°, 13.720±0.2°, 15.285±0.2°, 16.525±0.2°, 18.458±0.2°, 19.302±0.2°, 20.852±0.2°, 22.345±0.2°, 24.772±0.2°, 25.230±0.2°, 25.996±0.2°, 27.285±0.2°, 28.303±0.2°, 28.829±0.2°, 29.699±0.2°, 30.703±0.2°, 33.133±0.2°, 34.655±0.2°, 36.829±0.2°; and 37.967±0.2°,

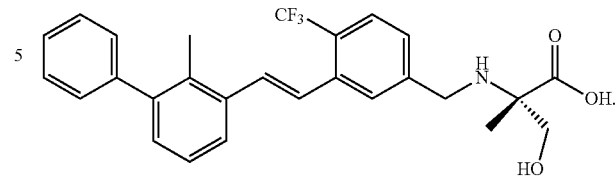

6. The crystal form C of the compound as shown in formula I as defined in claim 5, wherein, in the X-ray powder diffraction pattern of the crystal form C represented by 2θ angles, the 2θ values are as shown in the following table,

| 2θ (2θ ± 0.2°) | Relative intensity (%) |
|---|---|
| 6.250 | 100 |
| 6.979 | 15.3 |
| 8.779 | 38.6 |
| 12.635 | 21.3 |
| 13.720 | 32.6 |
| 15.285 | 3.1 |
| 16.525 | 24.1 |
| 17.696 | 5.5 |
| 18.458 | 73.0 |
| 19.302 | 59.0 |
| 20.852 | 15.4 |
| 22.345 | 19.1 |
| 24.772 | 14.3 |
| 25.230 | 11.5 |
| 25.996 | 4.1 |
| 27.285 | 13.2 |
| 28.303 | 4.1 |
| 28.829 | 3.7 |
| 29.699 | 2.3 |
| 30.703 | 5.6 |
| 33.133 | 3.1 |
| 34.655 | 1.9 |
| 36.829 | 2.4 |
| 37.967 | 3.1; | or, in the differential scanning calorimetry analysis of the crystal form C, the differential scanning calorimetry analysis of the crystal form C has a thermal absorption peak at 243° C., and the melting heat is 99.33 J/g;

or, in the thermogravimetric analysis of the crystal form C, the sample has a weight loss of 0.62% from 24.0° C. to 58.0° C., and the sample has a weight loss of 2.5% from 58.0° C. to 162.3° C., and the "%" is the weight percentage;

or, in the dynamic vapor sorption analysis of the crystal form C, the sample has a weight gain of 4.767% from 0% RH to 95% RH.

7. The crystal form A of the compound as shown in formula I as defined in claim 1, wherein the polarized light micrograph of the crystal form A is as shown in FIG. 1;

or, the differential scanning calorimetry analysis pattern of the crystal form A is as shown in FIG. 2;

or, the thermogravimetric analysis pattern of the crystal form A is as shown in FIG. 3;

or, the X-ray powder diffraction pattern of the crystal form A is as shown in FIG. 4;

or, the dynamic vapor sorption analysis pattern of the crystal form A is as shown in FIG. 5.

8. A method of preparing the crystal form A of the compound as shown in formula I as defined in claim 1, comprising the following steps: in a solvent, crystallizing the compound as shown in formula I; the crystallization method is suspension equilibrium method, solution heating-slow cooling method or anti-solvent method; the solvent is ethanol, and when the crystallization method is anti-solvent method, the anti-solvent is an alkane solvent.

9. The method of preparing the crystal form A of the compound as shown in formula I as defined in claim 8, wherein, the crystallization temperature is 20° C. to 60° C.;
or, when the crystallization method is anti-solvent method, the alkane solvent is $C_{1-10}$ alkane solvent;
or, the mass-volume ratio of the compound as shown in formula I to the solvent is 5 mg/mL to 20 mg/mL;
or, the crystallization time is 1 hour to 20 days;
or, when the crystallization method is anti-solvent method, the mass ratio of the anti-solvent to the solvent is 5:1 to 8:1.

10. A method of preparing the crystal form B of the compound as shown in formula I as defined in claim 3, comprising the following steps: in a solvent, crystallizing the compound as shown in formula I; the crystallization method is suspension equilibrium method or anti-solvent method; when the crystallization method is suspension equilibrium method, the solvent is water, or ethanol and water; and when the crystallization method is anti-solvent method, the solvent is ethanol or tetrahydrofuran, and the anti-solvent is water.

11. The method of preparing the crystal form B of the compound as shown in formula I as defined in claim 10, wherein, the water is one or more of distilled water, deionized water, purified water, tap water and mineral water;
or, the crystallization temperature is 20° C. to 60° C.;
or, the mass-volume ratio of the compound as shown in formula I to the solvent is 5 mg/mL to 40 mg/mL;
or, the crystallization time is 1 hour to 20 days;
or, when the crystallization method is suspension equilibrium method, and when the solvent is ethanol and water, the volume ratio of ethanol to water is 1:3 to 1:5;
or, when the crystallization method is anti-solvent method, the volume ratio of the anti-solvent to the solvent is 1:1 to 4:1.

12. A method of preparing the crystal form C of the compound as shown in formula I as defined in claim 5, comprising the following steps: in a solvent, crystallizing the compound as shown in formula I by suspension equilibrium method; the solvent is isopropanol, N,N-dimethylacetamide, or acetone and water.

13. The method of preparing the crystal form C of the compound as shown in formula I as defined in claim 12, wherein, the water is one or more of distilled water, deionized water, purified water, tap water and mineral water;
or, when the solvent is acetone and water, the volume ratio of acetone to water is 7:1 to 10:1;
or, the crystallization temperature is room temperature;
or, the mass-volume ratio of the compound as shown in formula I to the solvent is 10 mg/mL to 50 mg/mL;
or, the crystallization time is 1 day to 20 days.

14. A method for treating cancer in a subject in need thereof, comprising: administering an effective amount of the crystal form A of the compound as shown in formula I as defined in claim 1 to the subject; the cancer is one or more of lung cancer, esophageal cancer, gastric cancer, colorectal cancer, liver cancer, nasopharyngeal cancer, brain tumor, breast cancer, cervical cancer, blood cancer and bone cancer.

15. The crystal form B of the compound as shown in formula I as defined in claim 3, wherein the X-ray powder diffraction pattern of the crystal form B is as shown in FIG. 6;

or, the differential scanning calorimetry analysis pattern of the crystal form B is as shown in FIG. 7;
or, the thermogravimetric analysis pattern of the crystal form B is as shown in FIG. 8;
or, the dynamic vapor sorption analysis pattern of the crystal form B is as shown in FIG. 9.

16. The crystal form C of the compound as shown in formula I as defined in claim 5, wherein the X-ray powder diffraction pattern of the crystal form C is as shown in FIG. 10;
or, the differential scanning calorimetry analysis pattern of the crystal form C is as shown in FIG. 11;
or, the thermogravimetric analysis pattern of the crystal form C is as shown in FIG. 12;
or, the dynamic vapor sorption analysis pattern of the crystal form C is as shown in FIG. 13.

17. A method for treating cancer in a subject in need thereof, comprising: administering an effective amount of the crystal form B of the compound as shown in formula I as defined in claim 3 to the subject; the cancer is one or more of lung cancer, esophageal cancer, gastric cancer, colorectal cancer, liver cancer, nasopharyngeal cancer, brain tumor, breast cancer, cervical cancer, blood cancer and bone cancer.

18. A method for treating cancer in a subject in need thereof, comprising: administering an effective amount of the crystal form C of the compound as shown in formula I as defined in claim 5 to the subject; the cancer is one or more of lung cancer, esophageal cancer, gastric cancer, colorectal cancer, liver cancer, nasopharyngeal cancer, brain tumor, breast cancer, cervical cancer, blood cancer and bone cancer.

19. The method of preparing the crystal form A of the compound as shown in formula I as defined in claim 9, wherein, the crystallization temperature is room temperature or 50° C.;
or, when the crystallization method is anti-solvent method, the alkane solvent is n-heptane;
or, the mass-volume ratio of the compound as shown in formula I to the solvent is 7.7 mg/mL to 20 mg/mL;
or, the crystallization time is 1 hour to 2 hours, 5 hours to 6 hours or 10 days to 20 days;
or, when the crystallization method is anti-solvent method, the mass ratio of the anti-solvent to the solvent is 6.5:1.

20. The method of preparing the crystal form B of the compound as shown in formula I as defined in claim 11, wherein, the crystallization temperature is room temperature or 50° C.;
or, the mass-volume ratio of the compound as shown in formula I to the solvent is 7.7 mg/mL, 11.1 mg/mL, 20 mg/mL or 33.3 mg/mL;
or, the crystallization time is 1 hour to 2 hours, 1 day or 17 days;
or, when the crystallization method is suspension equilibrium method, and when the solvent is ethanol and water, the volume ratio of ethanol to water is 1:4;
or, when the crystallization method is anti-solvent method, the volume ratio of the anti-solvent to the solvent is 1:1 or 2.7:1.

21. The method of preparing the crystal form C of the compound as shown in formula I as defined in claim 13, wherein, when the solvent is acetone and water, the volume ratio of acetone to water is 8:1;

or, the mass-volume ratio of the compound as shown in formula I to the solvent is 20 mg/mL, 40 mg/mL or 44.4 mg/mL;

or, the crystallization time is 1 day, 7 days, 10 days or 20 days.

* * * * *

UNITED STATES PATENT AND TRADEMARK OFFICE
CERTIFICATE OF CORRECTION

PATENT NO. : 12,428,369 B2
APPLICATION NO. : 17/912142
DATED : September 30, 2025
INVENTOR(S) : Yuguang Wang, Nong Zhang and Pingjing Zhang It is certified that error appears in the above-identified patent and that said Letters Patent is hereby corrected as shown below:

In the Claims

Claim 2, Column 25, Line 54, please delete the phrase "by 2θ angles, the 20 values" and replace with "by 2θ angles, the 2θ values".

Claim 6, Column 28, Line 15, please delete the phrase "by 2θ angles, the 20 values" and replace with "by 2θ angles, the 2θ values".

Signed and Sealed this
Ninth Day of December, 2025

John A. Squires
*Director of the United States Patent and Trademark Office*